US007071311B2

(12) United States Patent
Radka et al.

(10) Patent No.: US 7,071,311 B2
(45) Date of Patent: Jul. 4, 2006

(54) ANTIBODIES HAVING SPECIFICITY FOR 2'-C-ALLYL NUCLEIC ACIDS

(75) Inventors: Susan Radka, Arvada, CO (US); Leonid Beigelman, Longmont, CO (US); Haeberli Peter, Berthoud, CO (US)

(73) Assignee: Sirna Therapeutics, Inc., Boulder, CO (US)

( * ) Notice: Subject to any disclaimer, the term of this patent is extended or adjusted under 35 U.S.C. 154(b) by 363 days.

(21) Appl. No.: 10/366,191

(22) Filed: Feb. 12, 2003

(65) Prior Publication Data

US 2003/0228590 A1 Dec. 11, 2003

Related U.S. Application Data

(60) Provisional application No. 60/356,298, filed on Feb. 13, 2002.

(51) Int. Cl.
*C07K 16/00* (2006.01)
*C12P 21/04* (2006.01)
*A61K 39/395* (2006.01)
*C07H 21/04* (2006.01)

(52) U.S. Cl. .............................. 530/388.1; 530/387.1; 530/388.21; 424/130.1; 424/141.1; 536/24.5; 435/70.21

(58) Field of Classification Search ............ 530/387.1, 530/388.1, 388.21; 424/130.1, 141.1; 536/24.5; 435/70.21
See application file for complete search history.

(56) References Cited

U.S. PATENT DOCUMENTS

| | | | |
|---|---|---|---|
| 4,987,071 | A | 1/1991 | Cech et al. |
| 5,028,524 | A | 7/1991 | Fujisawa et al. |
| 5,395,938 | A | 3/1995 | Ramakrishnan |
| 5,589,332 | A | 12/1996 | Shih et al. |
| 5,672,695 | A | 9/1997 | Eckstein et al. |
| 5,741,679 | A | 4/1998 | George et al. |
| 5,767,263 | A | 6/1998 | Usman et al. |
| 5,807,718 | A | 9/1998 | Joyce et al. |
| 5,834,186 | A | 11/1998 | George et al. |
| 5,849,902 | A | 12/1998 | Arrow et al. |
| 5,871,914 | A | 2/1999 | Nathan et al. |
| 5,989,912 | A | 11/1999 | Arrow et al. |
| 5,998,203 | A | 12/1999 | Matulic-Adamic |
| 6,001,311 | A | 12/1999 | Brennan |
| 6,087,188 | A | 7/2000 | Johansen et al. |
| 6,127,173 | A | 10/2000 | Eckstein et al. |
| 6,159,714 | A | 12/2000 | Usman et al. |
| 6,342,221 | B1 | 1/2002 | Thorpe et al. |

FOREIGN PATENT DOCUMENTS

| | | |
|---|---|---|
| WO | WO 93/23569 | 11/1993 |
| WO | WO 96/10390 | 4/1996 |
| WO | WO 96/10391 | 4/1996 |
| WO | WO 96/10392 | 4/1996 |
| WO | WO 97/26270 | 7/1997 |
| WO | WO 98/27104 | 6/1998 |
| WO | WO 98/58058 | 12/1998 |
| WO | WO 99/29842 | 6/1999 |
| WO | WO 99/54459 | 10/1999 |
| WO | WO 99/55857 | 11/1999 |
| WO | WO 00/24931 | 5/2000 |
| WO | WO 00/26226 | 5/2000 |

OTHER PUBLICATIONS

Reines D. Analytical Biochemistry, 196(2):367-372, Aug. 1, 1991.*

Shefner et al. Journal of Experimental Medicine 173:287-296, Feb. 1991.*

Radka et al. Analytical Biochemistry, 307(1):40-46, Aug. 1, 2002.*

U.S. Appl. No. 09/800,594, filed Mar. 6, 2001, Usman et al.

U.S. Appl. No. 10/201,394, filed Jul. 22, 2002, Vargeese et al.

U.S. Appl. No. 08/878,640, filed Mar. 6, 2001, Ludwig et al.

U.S. Appl. No. 09/476,387, filed Dec. 30, 1999, Beigelman et al.

U.S. Appl. No. 09/918,728, filed Jul. 31, 2001, Beigelman et al.

U.S. Appl. No. 08/878,640, filed Mar. 6, 2001, Ludwig et al.

Bass, "The short answer," *Nature* 411:428-429 (2001).

Beigelman et al., "Synthesis of 2'-modified nucleotides and their incorporation into hammerhead ribozymes," *Nucleic Acids Research* 23(21):4434-4442 (1995).

Bellon et al., "Amino-Linked Ribozymes: Post-Synthetic Conjugation of Half-Ribozymes," *Nucleosides & Nucleotides* 16:951-954 (1997).

Bellon et al., "Post-synthetically Ligated Ribozymes: An Alternative Approach to Iterative Solid Phase Synthesis," *Bioconjugate Chem.* 8:204-212 (1997).

Breaker et al., "A DNA enzyme with $Mg^2$-dependent RNA phosphoesterase activity," *Chemistry & Biology* 2(10):655-660 (1995).

(Continued)

*Primary Examiner*—Larry R. Helms
*Assistant Examiner*—David J. Blanchard
(74) *Attorney, Agent, or Firm*—McDonnell Boehnen Hulbert & Berghoff, LLP

(57) ABSTRACT

The present invention relates to antibodies, antibody conjugates, and compositions thereof, methods of antibody synthesis, and applications of antibodies useful for detecting the presence of nucleic acid molecules in vivo, such as in a clinical setting. The antibodies of the invention are also useful as screening agents which allow the selection of candidate therapeutic molecules for optimum bioavailability and/or activity, and as delivery agents for cell and tissue specific delivery of nucleic acid molecules.

16 Claims, 11 Drawing Sheets

OTHER PUBLICATIONS

Breaker, "Are engineered proteins getting competiton from RNA?" *Current Opinion in Biotechnology* 7:442-448 (1996).
Breaker, "Catalytic DNA: in training and seeking employment," *Nature Biotechnology* 17:422-423 (1999).
Brennan et al., "Two-Dimensional Parallel Array Technology as a New Approach to Automated Combinatorial Solid-Phase Organic Synthesis," *Biotechnology and Bioengineering* (*Combinatorial Chemistry*) 61:33-45 (1998).
Brody and Gold, "Aptamers as therapeutic and diagnostic agents," *Reviews in Molecular Biotechnology* 74:5-13 (2000).
Burgin et al., "Chemically Modified Hammerhead Ribozymes with improved Catalytic Rates," *Biochemistry* 35:14090-14097 (1996) (volume no. mistakenly listed as 6).
Caruthers et al., "Chemical Synthesis of Deoxyoligonucleotides and Deoxyoligonucleotide Analogs," *Methods in Enzymology* 211:3-19 (1992).
Cech, "Ribozymes and Their Medical Implications," *JAMA* 260:3030-3034 (1988).
Chartrand et al., "An oligodeoxyribonucleotide that supports catalytic activity in the hammerhead ribozyme domain," *Nucleic Acids Research* 23(20):4092-4096 (1995).
Crooke et al., "Antisens '97: A roundtable on the state of the idustry," *Nature Biotechnology* 15:519-524 (1997).
Crooke, "Advances in Understanding the Pharmacological Properties of Antisense Oligonucleotides," *Advances in Pharmacology* 40:1-49 (1997).
Crooke, "Antisense Therapeutics," *Biotechnology and Genetic Engineering Reviews* 15:121-157 (1998).
Crooke, "Progress in Antisense Technology: The End of the Beginning," *Methods in Enzymology* 313:3-45 (1999).
Delihas et al., "Natural antisense RNA/target RNA interactions: Possible models for antisense oligonucleotide drug design," *Nature Biotechnology* 15:751-753 (1997).
Duval-Valentin, "Specific inhibition of transcription by triple helix-forming oligonucleotides," *Proc. Natl. Acad. Sci. USA* 89:504-508 (1992).
Egholm et al., "PNA hybridizes to complementary oligonucleotides obeying the Watson-Crick hydrogen-bonding rules," *Nature* 365:566-568 (1993).
Elibashir et al., "Duplexes of 21-nucleotide RNAs mediate RNA interference in cultured mammalian cells," *Nature* 411:494-498 (2001).
Fox, "Targeting DNA with Triplexes," *Current Medicinal Chemistry* 7:17-37 (2000).
Freier et al., "Improved free-energy parameters for predictions of RNA duplex stability," *Proc. Natl. Acad. Sci. USA* 83:9373-9377 (1986) [sometimes referred to as Frier].
Gold et al., "Diversity of Oligonucleotide Functions," *Annu. Rev. Biochem.* 64:763-797 (1995).
Halloran and Parker, "The Preparation of Nucleotide-Protein Conjugates: Carbodiimides as Coupling Agents," *Journal of Immunology* 96:373-378 (1966).
Hammann et al., "Length Variation of Helix III in a Hammerhead Ribozyme and its Influence on Cleavage Activity," *Antisense & Nucleic Acid Drug Development* 9:25-31 (1999).
Hermnn and Patel, "Adaptive Recognition by Nucleic Acid Aptamers," *Science* 287:820-825 (2000).
Hertel et al., "Numbering System for the Hammerhead," *Nucleic Acids Research* 20:3252 (1992).
Ishiwata et al., "Physical-Chemistry Characteristics and Biodistribution of Poly(ethylene glycol)-Coated Liposomes Using Poly(oxyethylene) Cholesteryl Ether," *Chem. Pharm. Bull.* 43:1005-1011 (1995) (mistakenly referred to as Ishiwataet).
Jayasena, "Aptamers: An Emerging Class of Molecules that Rival Antibodies in Diagnostics," *Clinical Chemistry* 45:1628-1650 (1999).
Kearney et al., "A New Mouse Myeloma Cell Line That Has Lost Immunoglobulin Expression but Permits the Construction of Antibody-Secreting Hybrid Cell Lines," *Journal of Immunology* 123:1548-1550 (1979).
Kore, et al., "Sequence specificity of the hammmerhead ribozyme revisistsed; the NIH rule," *Nucleic Acids Research*, 26(18):4116-4120 (1998).
Kusser, "Chemically modified nucleic acid aptamers for in vitro selections: evolving evolution," *Reviews in Molecular Biotechnology* 74:27-38 (2000).
Lasic and Needham "The 'Stealth' Liposome: A Prototypical Biomaterial," *Chemical Reviews* 95:2601-2627 (1995).
Lasic and Papahadjopoulaos, "Liposomes Revisited," *Science* 267:1275-1276 (1995).
Limbach et al., "Summary: the modified nucleosides of RNA," *Nucleic Acids Research* 22(12):2183-2196 (1994).
Liu et al., "Cationic Liposome-mediated Intravenous Gene Delivery," *J. Biol. Chem.* 270(42):24864-24870 (1995).
Moore and Sharp, "Site-Specific Modification of Pre-mRNA: The 2'-Hydroxyl Groups at the Splice Sites," *Science* 256:992-996 (1992).
Oku et al., "Real-time analysis of liposomal trafficking in tumor-bearing mice by use of positron emission tomography," *Biochimica et Biophysica Acta* 1238:86-90 (1995).
Player and Torrence, "The 2-5A System: Modulation of Viral and Cellular Processes Through Acceleration of RNA Degradation," *Pharmacol Ther.* 78:55-113 (1998).
Praseuth et al., "Triple helix formation and the antigene for sequence-specific control of gene expression," *Biochimica et Biophysica Acta* 1489:181-206 (1999).
Santoro and Joyce, "A general purpose RNA-cleaving DNA enzyme," *Proc. Natl. Acad. Sci. USA* 94:4262-4266 (1997).
Santoro et al., "RNA Cleavage by a DNA Enzyme with Extended Chemical Functionality," *J. Am. Chem. Soc.* 122:2433-2439 (2000).
Scaringe et al., "Chemical synthesis of biologically active oligoribonucleotides using β-cyanoethyl protected ribonucleoside phosphoramidites," *Nucl Acids Res.* 18:5433-5441 (1990).
Schmajuk et al., "Antisense Oligonucleotides with Different Backbones," *The Journal of Biological Chemistry* 274:21783-21789 (1999).
Shabarova et al., "Chemical ligation of DNA: The first non-enyzmatic assembly of a biologically active gene," *Nucleic Acids Research* 19:4247-4251 (1991).
Silverman et al., "Selective RNA Cleavage by Isolated RNase L Activated with 2-5A Antisense Chimeric Oligonucleotides," *Methods in Enzymology* 313:522-533 (1999).
Stein and Cheng, "Antisense Oligonucleotides as Therapeutic Agents—Is the Bullet Really Magical?" *Science* 261:1004-1288 (1993).
Stein et al., "A Specificity Comparison of Four Antisense Types: Morpholino, 2'-O-Methyl RNA, DNA, and Phosphorothioate DNA," *Antisense & Nucleic Acid Drug Development* 7:151-157 (1997).

Sullenger et al., "Overexpression of TAR Sequences Renders Cells Resistant to Human Immunodeficiency Virus Replication," *Cell* 63:601-608 (1990).
Sun, "Technology evaluation: SELEX, Giliad Sciences Inc," *Current Opinion in Molecular Therapeutics* 2:100-105 (2000).
Torrence et al., "Targeting RNA for degradation with a (2'-5') oligoadenylate-antisense chimera," *Proc. Natl. Acad. Sci. USA* 90:1300-1304 (1993).
Turner et al., "Improved Parameters for Prediction of RNA Structure," *Cold Spring Harbor Symposia on Quantitative Biology* vol. LII, pp. 123-133 (1987).
Turner et al., "Free Energy Increments for Hydrogen Bonds in Nucleic Acid Base Pairs," *J. Am. Chem. Soc.* 109:3783-3785 (1987).
Usman and Cedergren, "Exploiting the chemical synthesis of RNA," *TIBS* 17:334-339 (1992).
Usman et al., "Automated Chemical Synthesis of Long Oligoribonucleotides Using 2'-O-Silylated Ribonucleoside 3'-O-Phosphoramidites on a Controlled-Pore Glass Support: Synthesis of a 43-Nucleotide Sequence Similar to the 3'-Half Molecule of an *Escherichia coli* Formylmethoionine tRNA," *J. Am. Chem. Soc.* 109:7845-7854 (1987).
Usman et al., "Chemical modification of hammerhead ribozymes: activity and nuclease resistance," *Nucleic Acids Syposium Series* 31:163-164 (1994).
Usman et al., "Hammerhead ribozyme engineering," *Current Opinion in Structural Biology* 1:527-533(1996).
Werner and Uhlenbeck, "The effect of base mismatches in the substrate recognition helices of hammerhead ribozymes on binding and catalysis," *Nucleic Acids Research* 23:2092-2096 (1995).
Wincott et al., "Synthesis, deprotection, analysis and purification of RNA and ribozymes," *Nucleic Acids Research* 23(14):2677-2684 (1995).
Wincott et al., "Synthesis, deprotection, analysis and purification of RNA and ribozymes," *Nucleic Acids Research* 23(14):2677-2684 (1995).
Wincott et al., "A Practical Method for the Production of RNA and Ribozymes," *Methods in Molecular Biology* 74:59-69 (1997).
Yoshikawa et al., "Studies of Phosphorylation. III. Selective Phosphorylation of Unprotected Nucleosides," *Bulletin of the Chemical Society of Japan* 42:3505-3508 (1969).

* cited by examiner

Figure 1
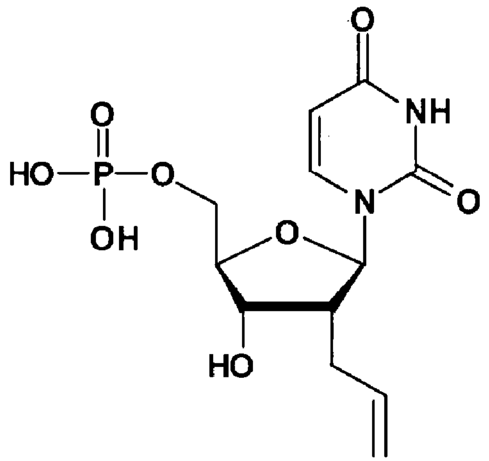
1
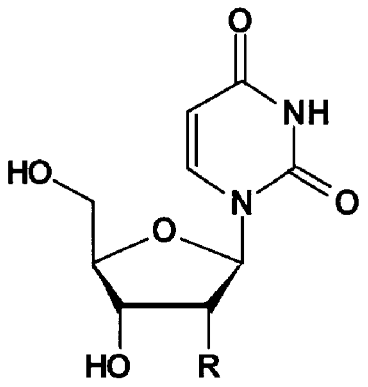
2. R = $NH_2$
3. R = $OCH_3$
4. R = H
5. R = $OCH_2$-CH=$CH_2$
6. R = $CH_2CH_2CH_3$
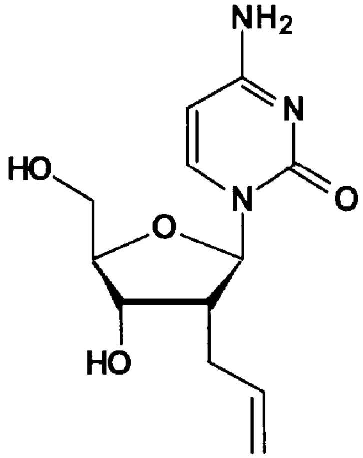
7

ANGIOZYME™

Uppercase: ribonucleotide

Lowercase: 2'-O-Me nucleotide

U: 2'-deoxy-2'-C-allyl Uridine

B: inverted 2'-deoxyribose abasic

S: phosphorothioate linkage

*Figure 6: Examples of Nuclease Stable Ribozyme Motifs*

*Figure 7: 2'-O-Me substituted Amberzyme Enzymatic Nucleic Acid Motif*

*Figure 8: Stabilized Zinzyme Ribozyme Motif*

Legend

Uppercase: indicates natural ribo residues

C : indicates 2'-deoxy-2'-amino Cytidine

Lowercase: 2'-O-methyl

S: phosphorothioate/phosphorodithioate linkage

B: 3'-3' abasic moiety

*Figure 9: DNAzyme Motif*

Uppercase: ribonucleotide
Lowercase: 2'-*O*-Me nucleotide
U: 2' C-allyl U nucleotide
B: inverted 2'-deoxyribose abasic
s: phosphorothioate linkage

SEQUENCE LISTING

```
<160> NUMBER OF SEQ ID NOS: 17

<210> SEQ ID NO 1
<211> LENGTH: 34
<212> TYPE: RNA
<213> ORGANISM: Artificial Sequence
<220> FEATURE:
<223> OTHER INFORMATION: Description of Artificial Sequence:
      Enzymatic Nucleic Acid
```

-continued

<220> FEATURE:
<221> NAME/KEY: misc_feature
<222> LOCATION: (1)..(4)
<223> OTHER INFORMATION: Phosphorothioate 3'-Internucleotide Linkage
<220> FEATURE:
<221> NAME/KEY: misc_feature
<222> LOCATION: (1)..(7)
<223> OTHER INFORMATION: 2'-O-Methyl
<220> FEATURE:
<221> NAME/KEY: misc_feature
<222> LOCATION: (11)..(11)
<223> OTHER INFORMATION: 2'-O-Methyl
<220> FEATURE:
<221> NAME/KEY: misc_feature
<222> LOCATION: (13)..(25)
<223> OTHER INFORMATION: 2'-O-Methyl
<220> FEATURE:
<221> NAME/KEY: misc_feature
<222> LOCATION: (27)..(28)
<223> OTHER INFORMATION: 2'-O-Methyl
<220> FEATURE:
<221> NAME/KEY: misc_feature
<222> LOCATION: (30)..(34)
<223> OTHER INFORMATION: 2'-O-Methyl
<220> FEATURE:
<221> NAME/KEY: misc_feature
<222> LOCATION: (8)..(8)
<223> OTHER INFORMATION: 2'-deoxy-2'-C-allyl
<220> FEATURE:
<221> NAME/KEY: misc_feature
<222> LOCATION: (34)..(34)
<223> OTHER INFORMATION: 3'-end phosphate attached to an inverted deoxyabasic moiety, in a 3'-3 orientation

<400> SEQUENCE: 1
gaguugcuga ugaggccgaa aggccgaaag ucug 34

<210> SEQ ID NO 2
<211> LENGTH: 13
<212> TYPE: RNA
<213> ORGANISM: Homo Sapien

<400> SEQUENCE: 2
ugagcugcac ugc 13

<210> SEQ ID NO 3
<211> LENGTH: 33
<212> TYPE: RNA
<213> ORGANISM: Artificial Sequence
<220> FEATURE:
<223> OTHER INFORMATION: Description of Artificial Sequence: Enzymatic Nucleic Acid
<220> FEATURE:
<221> NAME/KEY: misc_feature
<222> LOCATION: (1)..(4)
<223> OTHER INFORMATION: Phosphorothioate 3'-Internucleotide Linkage
<220> FEATURE:
<221> NAME/KEY: misc_feature
<222> LOCATION: (1)..(15)
<223> OTHER INFORMATION: 2'-O-Methyl
<220> FEATURE:
<221> NAME/KEY: misc_feature
<222> LOCATION: (17)..(22)
<223> OTHER INFORMATION: 2'-O-Methyl
<220> FEATURE:
<221> NAME/KEY: misc_feature
<222> LOCATION: (25)..(25)
<223> OTHER INFORMATION: 2'-O-Methyl
<220> FEATURE:
<221> NAME/KEY: misc_feature
<222> LOCATION: (27)..(33)
<223> OTHER INFORMATION: 2'-O-Methyl
<220> FEATURE:
<221> NAME/KEY: misc_feature
<222> LOCATION: (16)..(16)

-continued

```
<223> OTHER INFORMATION: 2'-deoxy-2'-amino
<220> FEATURE:
<221> NAME/KEY: misc_feature
<222> LOCATION: (26)..(26)
<223> OTHER INFORMATION: 2'-deoxy-2'-amino
<220> FEATURE:
<221> NAME/KEY: misc_feature
<222> LOCATION: (33)..(33)
<223> OTHER INFORMATION: 3'-end phosphate attached to an inverted
      deoxyabasic moiety, in a 3'-3 orientation

<400> SEQUENCE: 3

gcaguggccg aaaggcgagu gaggucuagc uca                              33


<210> SEQ ID NO 4
<211> LENGTH: 15
<212> TYPE: RNA
<213> ORGANISM: Artificial Sequence
<220> FEATURE:
<223> OTHER INFORMATION: Description of Artificial Sequence:
      Nucleic Acid Substrate
<220> FEATURE:
<221> NAME/KEY: misc_feature
<222> LOCATION: (1)..(6)
<223> OTHER INFORMATION: n stands for a, c, g, or u
<220> FEATURE:
<221> NAME/KEY: misc_feature
<222> LOCATION: (9)..(15)
<223> OTHER INFORMATION: n stands for a, c, g, or u

<400> SEQUENCE: 4

nnnnnnuhnn nnnnn                                                  15


<210> SEQ ID NO 5
<211> LENGTH: 36
<212> TYPE: RNA
<213> ORGANISM: Artificial Sequence
<220> FEATURE:
<223> OTHER INFORMATION: Description of Artificial Sequence:
      Enzymatic Nucleic Acid
<220> FEATURE:
<221> NAME/KEY: misc_feature
<222> LOCATION: (1)..(7)
<223> OTHER INFORMATION: n stands for a, c, g, or u
<220> FEATURE:
<221> NAME/KEY: misc_feature
<222> LOCATION: (16)..(18)
<223> OTHER INFORMATION: n stands for a, c, g, or u
<220> FEATURE:
<221> NAME/KEY: misc_feature
<222> LOCATION: (23)..(25)
<223> OTHER INFORMATION: n stands for a, c, g, or u
<220> FEATURE:
<221> NAME/KEY: misc_feature
<222> LOCATION: (31)..(36)
<223> OTHER INFORMATION: n stands for a, c, g, or u
<220> FEATURE:
<221> NAME/KEY: misc_feature
<222> LOCATION: (1)..(8)
<223> OTHER INFORMATION: 2'-O-Methyl
<220> FEATURE:
<221> NAME/KEY: misc_feature
<222> LOCATION: (12)..(12)
<223> OTHER INFORMATION: 2'-O-Methyl
<220> FEATURE:
<221> NAME/KEY: misc_feature
<222> LOCATION: (14)..(26)
<223> OTHER INFORMATION: 2'-O-Methyl
<220> FEATURE:
<221> NAME/KEY: misc_feature
<222> LOCATION: (28)..(29)
<223> OTHER INFORMATION: 2'-O-Methyl
<220> FEATURE:
<221> NAME/KEY: misc_feature
<222> LOCATION: (31)..(36)
```

-continued

<223> OTHER INFORMATION: 2'-O-Methyl
<220> FEATURE:
<221> NAME/KEY: misc_feature
<222> LOCATION: (9)..(9)
<223> OTHER INFORMATION: 2'-deoxy-2'-C-Allyl

<400> SEQUENCE: 5
nnnnnnncug augagnnnga aannncgaaa nnnnnn 36

<210> SEQ ID NO 6
<211> LENGTH: 14
<212> TYPE: RNA
<213> ORGANISM: Artificial Sequence
<220> FEATURE:
<223> OTHER INFORMATION: Description of Artificial Sequence:
Nucleic Acid Substrate
<220> FEATURE:
<221> NAME/KEY: misc_feature
<222> LOCATION: (1)..(5)
<223> OTHER INFORMATION: n stands for a, c, g, or u
<220> FEATURE:
<221> NAME/KEY: misc_feature
<222> LOCATION: (8)..(14)
<223> OTHER INFORMATION: n stands for a, c, g, or u

<400> SEQUENCE: 6
nnnnnchnnn nnnn 14

<210> SEQ ID NO 7
<211> LENGTH: 35
<212> TYPE: RNA
<213> ORGANISM: Artificial Sequence
<220> FEATURE:
<223> OTHER INFORMATION: Description of Artificial Sequence:
Enzymatic Nucleic Acid
<220> FEATURE:
<221> NAME/KEY: misc_feature
<222> LOCATION: (1)..(7)
<223> OTHER INFORMATION: n stands for a, c, g, or u
<220> FEATURE:
<221> NAME/KEY: misc_feature
<222> LOCATION: (16)..(18)
<223> OTHER INFORMATION: n stands for a, c, g, or u
<220> FEATURE:
<221> NAME/KEY: misc_feature
<222> LOCATION: (23)..(25)
<223> OTHER INFORMATION: n stands for a, c, g, or u
<220> FEATURE:
<221> NAME/KEY: misc_feature
<222> LOCATION: (31)..(35)
<223> OTHER INFORMATION: n stands for a, c, g, or u
<220> FEATURE:
<221> NAME/KEY: misc_feature
<222> LOCATION: (1)..(8)
<223> OTHER INFORMATION: 2'-O-Methyl
<220> FEATURE:
<221> NAME/KEY: misc_feature
<222> LOCATION: (12)..(12)
<223> OTHER INFORMATION: 2'-O-Methyl
<220> FEATURE:
<221> NAME/KEY: misc_feature
<222> LOCATION: (14)..(26)
<223> OTHER INFORMATION: 2'-O-Methyl
<220> FEATURE:
<221> NAME/KEY: misc_feature
<222> LOCATION: (28)..(29)
<223> OTHER INFORMATION: 2'-O-Methyl
<220> FEATURE:
<221> NAME/KEY: misc_feature
<222> LOCATION: (31)..(35)
<223> OTHER INFORMATION: 2'-O-Methyl
<220> FEATURE:
<221> NAME/KEY: misc_feature
<222> LOCATION: (30)..(30)
<223> OTHER INFORMATION: n stands for Inosine -continued

```
<220> FEATURE:
<221> NAME/KEY: misc_feature
<222> LOCATION: (9)..(9)
<223> OTHER INFORMATION: 2'-deoxy-2'-C-Allyl

<400> SEQUENCE: 7

nnnnnnncug augagnnnga aannncgaan nnnnn                              35


<210> SEQ ID NO 8
<211> LENGTH: 15
<212> TYPE: RNA
<213> ORGANISM: Artificial Sequence
<220> FEATURE:
<223> OTHER INFORMATION: Description of Artificial Sequence:
      Nucleic Acid Substrate
<220> FEATURE:
<221> NAME/KEY: misc_feature
<222> LOCATION: (1)..(6)
<223> OTHER INFORMATION: n stands for a, c, g, or u
<220> FEATURE:
<221> NAME/KEY: misc_feature
<222> LOCATION: (9)..(15)
<223> OTHER INFORMATION: n stands for a, c, g, or u

<400> SEQUENCE: 8

nnnnnnygnn nnnnn                                                    15


<210> SEQ ID NO 9
<211> LENGTH: 35
<212> TYPE: RNA
<213> ORGANISM: Artificial Sequence
<220> FEATURE:
<223> OTHER INFORMATION: Description of Artificial Sequence:
      Enzymatic Nucleic Acid
<220> FEATURE:
<221> NAME/KEY: misc_feature
<222> LOCATION: (1)..(7)
<223> OTHER INFORMATION: n stands for a, c, g, or u
<220> FEATURE:
<221> NAME/KEY: misc_feature
<222> LOCATION: (29)..(35)
<223> OTHER INFORMATION: n stands for a, c, g, or u
<220> FEATURE:
<221> NAME/KEY: misc_feature
<222> LOCATION: (1)..(8)
<223> OTHER INFORMATION: 2'-O-Methyl
<220> FEATURE:
<221> NAME/KEY: misc_feature
<222> LOCATION: (13)..(16)
<223> OTHER INFORMATION: 2'-O-Methyl
<220> FEATURE:
<221> NAME/KEY: misc_feature
<222> LOCATION: (18)..(35)
<223> OTHER INFORMATION: 2'-O-Methyl
<220> FEATURE:
<221> NAME/KEY: misc_feature
<222> LOCATION: (11)..(11)
<223> OTHER INFORMATION: Phosphorothioate 3'-Internucleotide Linkage

<400> SEQUENCE: 9

nnnnnnnuga uggcaugcac uaugcgcgnn nnnnn                              35


<210> SEQ ID NO 10
<211> LENGTH: 48
<212> TYPE: RNA
<213> ORGANISM: Artificial Sequence
<220> FEATURE:
<223> OTHER INFORMATION: Description of Artificial Sequence:
      Enzymatic Nucleic Acid
<220> FEATURE:
<221> NAME/KEY: misc_feature
<222> LOCATION: (1)..(8)
<223> OTHER INFORMATION: 2'-O-Methyl
```

-continued

```
<220> FEATURE:
<221> NAME/KEY: misc_feature
<222> LOCATION: (12)..(21)
<223> OTHER INFORMATION: 2'-O-Methyl
<220> FEATURE:
<221> NAME/KEY: misc_feature
<222> LOCATION: (32)..(37)
<223> OTHER INFORMATION: 2'-O-Methyl
<220> FEATURE:
<221> NAME/KEY: misc_feature
<222> LOCATION: (44)..(48)
<223> OTHER INFORMATION: 2'-O-Methyl
<220> FEATURE:
<221> NAME/KEY: misc_feature
<222> LOCATION: (9)..(10)
<223> OTHER INFORMATION: 2'-deoxy-2'-amino
<220> FEATURE:
<221> NAME/KEY: misc_feature
<222> LOCATION: (22)..(26)
<223> OTHER INFORMATION: 2'-deoxy-2'-amino
<220> FEATURE:
<221> NAME/KEY: misc_feature
<222> LOCATION: (38)..(40)
<223> OTHER INFORMATION: 2'-deoxy-2'-amino

<400> SEQUENCE: 10

gugugcaacc ggaggaaacu cccuucaagg acgaaagucc gggacggg                48


<210> SEQ ID NO 11
<211> LENGTH: 16
<212> TYPE: RNA
<213> ORGANISM: Homo sapien

<400> SEQUENCE: 11

gccguggguu gcacac                                                  16


<210> SEQ ID NO 12
<211> LENGTH: 35
<212> TYPE: RNA
<213> ORGANISM: Artificial Sequence
<220> FEATURE:
<223> OTHER INFORMATION: Description of Artificial Sequence:
      Enzymatic Nucleic Acid
<220> FEATURE:
<221> NAME/KEY: misc_feature
<222> LOCATION: (1)..(7)
<223> OTHER INFORMATION: 2'-O-Methyl
<220> FEATURE:
<221> NAME/KEY: misc_feature
<222> LOCATION: (9)..(15)
<223> OTHER INFORMATION: 2'-O-Methyl
<220> FEATURE:
<221> NAME/KEY: misc_feature
<222> LOCATION: (19)..(19)
<223> OTHER INFORMATION: 2'-O-Methyl
<220> FEATURE:
<221> NAME/KEY: misc_feature
<222> LOCATION: (21)..(21)
<223> OTHER INFORMATION: 2'-O-Methyl
<220> FEATURE:
<221> NAME/KEY: misc_feature
<222> LOCATION: (23)..(23)
<223> OTHER INFORMATION: 2'-O-Methyl
<220> FEATURE:
<221> NAME/KEY: misc_feature
<222> LOCATION: (26)..(26)
<223> OTHER INFORMATION: 2'-O-Methyl
<220> FEATURE:
<221> NAME/KEY: misc_feature
<222> LOCATION: (28)..(35)
<223> OTHER INFORMATION: 2'-O-Methyl
<220> FEATURE:
<221> NAME/KEY: misc_feature
<222> LOCATION: (1)..(4)
<223> OTHER INFORMATION: Phosphorothioate 3'-Internucleotide Linkage
```

-continued

<220> FEATURE:
<221> NAME/KEY: misc_feature
<222> LOCATION: (17)..(17)
<223> OTHER INFORMATION: 2'-deoxy-2'-amino
<220> FEATURE:
<221> NAME/KEY: misc_feature
<222> LOCATION: (27)..(27)
<223> OTHER INFORMATION: 2'-deoxy-2'-amino
<220> FEATURE:
<221> NAME/KEY: misc_feature
<222> LOCATION: (35)..(35)
<223> OTHER INFORMATION: 3'-end phosphate attached to an inverted deoxyabasic moiety, in a 3'-3 orientation

<400> SEQUENCE: 12
gugccuggcc gaaaggcgag ugaggucugc cgcgc 35

<210> SEQ ID NO 13
<211> LENGTH: 15
<212> TYPE: RNA
<213> ORGANISM: Homo sapiens

<400> SEQUENCE: 13
gcgcggcgca ggcac 15

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Enzymatic Nucleic Acid

<400> SEQUENCE: 14
rggctagcta caacga 16

<210> SEQ ID NO 15
<211> LENGTH: 13
<212> TYPE: RNA
<213> ORGANISM: Hepatitis C Virus

<400> SEQUENCE: 15
gguccuuucu ugg 13

<210> SEQ ID NO 16
<211> LENGTH: 32
<212> TYPE: RNA
<213> ORGANISM: Artificial Sequence
<220> FEATURE:
<221> NAME/KEY: misc_feature
<222> LOCATION: (1)..(4)
<223> OTHER INFORMATION: Phosphorothioate 3'-Internucleotide Linkage
<220> FEATURE:
<221> NAME/KEY: misc_feature
<222> LOCATION: (1)..(7)
<223> OTHER INFORMATION: 2'-O-Methyl
<220> FEATURE:
<221> NAME/KEY: misc_feature
<222> LOCATION: (11)..(11)
<223> OTHER INFORMATION: 2'-O-Methyl
<220> FEATURE:
<221> NAME/KEY: misc_feature
<222> LOCATION: (13)..(23)
<223> OTHER INFORMATION: 2'-O-Methyl
<220> FEATURE:
<221> NAME/KEY: misc_feature
<222> LOCATION: (25)..(26)
<223> OTHER INFORMATION: 2'-O-Methyl
<220> FEATURE:
<221> NAME/KEY: misc_feature
<222> LOCATION: (28)..(32)

-continued

```
<223> OTHER INFORMATION: 2'-O-Methyl
<220> FEATURE:
<221> NAME/KEY: misc_feature
<222> LOCATION: (8)..(8)
<223> OTHER INFORMATION: 2'-deoxy-2'-C-Allyl
<220> FEATURE:
<221> NAME/KEY: misc_feature
<222> LOCATION: (32)..(32)
<223> OTHER INFORMATION: 3'-end phosphate attached to an inverted
      deoxyabasic moiety, in a 3'-3 orientation

<400> SEQUENCE: 16


ccaagacuga ugaggcguua gccgaaagga cc                           32


<210> SEQ ID NO 17
<211> LENGTH: 36
<212> TYPE: RNA
<213> ORGANISM: Artificial Sequence
<220> FEATURE:
<223> OTHER INFORMATION: Description of Artificial Sequence:
      Enzymatic Nucleic Acid
<220> FEATURE:
<221> NAME/KEY: misc_feature
<222> LOCATION: (1)..(4)
<223> OTHER INFORMATION: Phosphorothioate 3'-Internucleotide Linkage
<220> FEATURE:
<221> NAME/KEY: misc_feature
<222> LOCATION: (1)..(8)
<223> OTHER INFORMATION: 2'-O-Methyl
<220> FEATURE:
<221> NAME/KEY: misc_feature
<222> LOCATION: (12)..(12)
<223> OTHER INFORMATION: 2'-O-Methyl
<220> FEATURE:
<221> NAME/KEY: misc_feature
<222> LOCATION: (14)..(26)
<223> OTHER INFORMATION: 2'-O-Methyl
<220> FEATURE:
<221> NAME/KEY: misc_feature
<222> LOCATION: (28)..(29)
<223> OTHER INFORMATION: 2'-O-Methyl
<220> FEATURE:
<221> NAME/KEY: misc_feature
<222> LOCATION: (31)..(36)
<223> OTHER INFORMATION: 2'-O-Methyl
<220> FEATURE:
<221> NAME/KEY: misc_feature
<222> LOCATION: (9)..(9)
<223> OTHER INFORMATION: 2'-C-Allyl
<220> FEATURE:
<221> NAME/KEY: misc_feature
<222> LOCATION: (36)..(36)
<223> OTHER INFORMATION: 3'-end phosphate attached to an inverted
      deoxyabasic moiety, in a 3'-3 orientation

<400> SEQUENCE: 17

gaaaauucug augaggccgu uaggccgaaa gagaag                       36
```

ANTIBODIES HAVING SPECIFICITY FOR 2'-C-ALLYL NUCLEIC ACIDS

This patent application claims the benefit of U.S. Provisional Patent Application No. 60/356,298, filed Feb. 13, 2002.

FIELD OF THE INVENTION

The present invention relates to antibodies, antibody-conjugates, compositions, methods of synthesis, and applications thereof. Specifically, the invention relates to monoclonal antibodies useful for detecting the presence of target nucleic acid molecules in vivo such as in a clinical setting. The antibodies of the invention are also useful as screening agents, which allow the selection of candidate therapeutic molecules for optimum bioavailability and/or activity, and as delivery agents for cell- and tissue-specific delivery of nucleic acid molecules.

BACKGROUND OF THE INVENTION

As therapeutic nucleic acid molecules begin to enter clinical trials, the need for methods of in vitro nucleic acid analysis and in vivo nucleic acid detection is essential. Thus, as nucleic acid therapeutics progress through preclinical studies and into clinical trials, there is a need for reagents capable of detecting such molecules in fluids (e.g., whole blood, plasma, spinal fluid and the like), cells, tissues, tissue samples and the like. For preclinical studies, addition of tags such as 2'-bromo-deoxyuridine (BrdU) and fluorescein to the nucleic acid molecule during synthesis is useful for localization studies. In clinical trials, however, nucleic acid molecules administered therapeutically do not carry such tags. Therefore, other methods of detection and analysis need to be developed in order to assay nucleic acid-based therapeutics in a bioanalytical clinical setting.

Antibodies are highly specific and efficient analytical tools that can be used in biomedical research. Modern researchers have capitalized on this bioanalytical tool through a variety of modification techniques, including antibody engineering using recombinant DNA methods. The use of antibodies has expanded from simple diagnostic assays to the detection of molecular structures, the elucidation of gene function, the localization of gene products, and the rapid screening of biological effectors for drug discovery and testing. The use of such antibodies with fluorescent or enzymatic tags, in concert with advances in microscopy, has resulted in improved enzyme-linked immunosorbent assay (ELISA) systems. The use of ELISA based microarrays with antibodies promises to transform current paradigms of disease research and the search for new therapeutic compounds. Moreover, antibodies can also serve not only as powerful research tools, but also as therapeutic compounds when conjugated with modifications such as radioisotopes and/or other chemotherapeutic compounds.

In recent years antibodies have become well characterized through experimentation and manipulation. The typical antibody is a tetrameric molecule comprising two copies of a heavy chain (H) polypeptide which is approximately 440 amino acids long and two copies of a light-chain (L) polypeptide which is about 220 amino acids long. Each antibody-based H and L polypeptide contains a variable region and a constant region. At the terminus of each arm of the Y-shaped antibody exists a site comprising the variable termini of the H and L subunits, which together bind to a specific and unique site on an antigen, otherwise known as an epitope. Antibody technology has developed from the production and use of polyclonal antibody mixtures derived from rabbits and horses to the production of specific monoclonal antibodies through cell fusion techniques using mice spleens and cancers, to modern engineering of uniquely designed mono and divalent antibodies. Chimeric antibodies are created when the antigen-binding component of a one antibody, such as a mouse antibody, is fused to the effector component of another antibody, for example a human antibody, using genetic engineering. Monoclonal antibodies originally raised in mice, rabbits, pigs, sheep, cows, horses or the like can also be "humanized" by exchanging surface-exposed amino acids, which can be determined through molecular biological (e.g., sequencing), crystallographic and molecular modeling techniques, found on the non-human antibody to those more often found in human antibodies. Also, mice have been developed that harbor human antibody-producing elements and major histocompatibility complexes (MHCs) in place of the corresponding murine elements and complexes, such that immunization of these mice leads to the direct generation of human antibodies in the mouse. Antibodies can also be fused with a variety of other proteins that can modulate both antibody activity and localization for specific applications.

The antibodies described herein are unique and distinct from previously described antibodies. Furthermore, antibodies of the present invention are useful in a variety of applications, including but not limited to bioanalytical assays supporting clinical trials, screening candidate therapeutic molecules for optimum bioavailability and/or activity in vivo, and the in vivo delivery of certain nucleic acid molecules to specific cells or tissues.

SUMMARY OF THE INVENTION

The present invention features antibodies and antibody conjugates and compositions to facilitate the analysis of nucleic acid molecules in a biological system, such as in cells, tissues, and in various organisms, for example humans. The antibodies provided by the instant invention also provide a useful tool for screening populations of nucleic acid molecules to determine optimum biological activity or bioavailability. The present invention also encompasses the site-specific delivery of nucleic acid molecules to particular cells and/or tissues. In general, the antibody-based transporters described are designed to be used either individually or as part of a multi-component system, with or without degradable linkers. The compounds of the invention described herein represent a useful bioanalytical tool for the analysis of therapeutic nucleic acid molecules in a clinical setting, as they can be used to screen for therapeutic nucleic acid molecules in vivo, and can be used to improve delivery of certain nucleic acid molecules to a number of cell types originating from different tissues.

In one embodiment, the invention features a monoclonal antibody (mAb) having binding affinity for nucleic acid molecules comprising a 2'-deoxy-2'-C-allyl Uridine nucleoside and/or nucleotide. In another embodiment, the monoclonal antibody (mAb) having binding affinity for nucleic acid molecules comprising a 2'-deoxy-2'-C-allyl Uridine nucleoside and/or nucleotide is a murine $IgGl_k$ antibody.

In another embodiment, the invention features a monoclonal antibody (mAb) having binding affinity for nucleic acid molecules comprising a nucleoside, nucleotide, or non-nucleotide having Formula I:

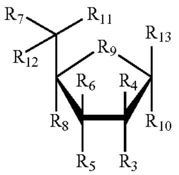

wherein each R3, R4, R5, R6, R7, R8, R10, R11 and R12 is independently H, OH, alkyl, substituted alkyl, alkaryl or aralkyl, F, Cl, Br, CN, CF3, OCF3, OCN, O-alkyl, S-alkyl, N-alkyl, O-alkenyl, S-alkenyl, N-alkenyl, SO-alkyl, alkyl-OSH, alkyl-OH, O-alkyl-OH, O-alkyl-SH, S-alkyl-OH, S-alkyl-SH, alkyl-S-alkyl, alkyl-O-alkyl, ONO2, NO2, N3, NH2, heterocycloalkyl, heterocycloalkaryl, aminoalkylamino, polyaklylamino, substituted silyl, or group having Formula II below; R9 is O, S, CH2, S=O, CHF, or CF2, and R13 is H or a nucleosidic base such as adenine, guanine, uracil, cytosine, thymine, 2-aminoadenosine, 5-methylcytosine, 2,6-diaminopurine, or any other non-naturally occurring base that can be employed to form a stable duplex with RNA or a non-nucleosidic base such as phenyl, naphthyl, 3-nitropyrrole, 5-nitroindole, nebularine, pyridone, pyridinone, or any other non-naturally occurring universal base that can be employed to form a stable duplex with RNA.

In another embodiment, the invention features a monoclonal antibody (mAb) having binding affinity for nucleotides and/or non-nucleotides of Formula I further comprising an internucleotide linkage having Formula II:

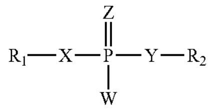

wherein each R1 and R2 is independently any nucleotide, non-nucleotide, or polynucleotide which can be naturally occurring or chemically modified, each X and Y is independently O, S, N, alkyl, or substituted alkyl, each Z and W is independently O, S, N, alkyl, substituted alkyl, O-alkyl, S-alkyl, alkaryl, or aralkyl, and wherein W, X, Y and Z are not all O.

In one embodiment, the invention features a monoclonal antibody (mAb) having binding affinity for a nucleic acid molecule comprising SEQ ID NO: 1. In another embodiment, the invention features a monoclonal antibody (mAb) having binding affinity for a nucleic acid molecule comprising SEQ ID NO: 3. In yet another embodiment, the invention features a monoclonal antibody (mAb) having binding affinity for a nucleic acid molecule comprising SEQ ID NO: 16. In another embodiment, the invention features a monoclonal antibody (mAb) having binding affinity for a nucleic acid molecule comprising SEQ ID NO: 17.

In one embodiment, the invention features a method for generating a monoclonal antibody (mAb) having binding affinity for nucleic acid molecules comprising a 2'-deoxy-2'-C-allyl Uridine nucleoside and/or nucleotide, comprising: (a) Conjugating a 2'-deoxy-2'-C-allyl Uridine nucleotide to a carrier protein, , to form a nucleotide-protein conjugate; (b) Immunizing a mammal with the conjugate from (a); (c) Obtaining antibody-producing cells from the immunized mammal of (b); (d) Fusing cells obtained from the mammal of (b) with myeloma cells under conditions suitable for generating a hybridoma; and (e) Isolating and using the supernatant from the hybridoma of (d) in a fusion screening assay suitable for isolating the monoclonal antibody. In one embodiment, the mammal used for immunization is a mouse. In one embodiment, the 2'-deoxy-2'-C-allyl Uridine nucleotide is a 2'-deoxy-2'-C-allyl Uridine 5'-phosphate.

In another embodiment, the invention features a method for generating a monoclonal antibody (mAb) having binding affinity for nucleic acid molecules comprising a nucleoside and/or nucleotide having Formula I, comprising: (a) a nucleoside and/or nucleotide having Formula I to a carrier protein, to form a nucleotide-protein conjugate; (b) Immunizing a mammal with the conjugate from (a); (c) Obtaining antibody-producing cells from the immunized mammal of (b); (d) Fusing cells obtained from the mammal of (b) with myeloma cells under conditions suitable for generating a hybridoma; and (e) Isolating and using the supernatant from the hybridoma of (d) in a fusion screening assay suitable for isolating the monoclonal antibody. In one embodiment, the mammal used for immunization is a mouse. In one embodiment, the nucleotide having Formula I is a nucleotide comprising a 5'-phosphate.

In another embodiment, the invention features a method for generating a monoclonal antibody (mAb) having binding affinity for a nucleic acid molecule having SEQ ID NO: 1, 3, 16, or 17, comprising: (a) Conjugating a nucleic acid molecule having SEQ ID NO: 1, 3, 16, or 17 to a carrier protein, to form a nucleic acid-protein conjugate; (b) Immunizing a mammal with the conjugate from (a); (c) Obtaining antibody-producing cells from the immunized mammal of (b); (d) Fusing cells obtained from the mammal of (b) with myeloma cells under conditions suitable for generating a hybridoma; and (e) Isolating and using supernatant from the hybridoma of (d) in a fusion screening assay suitable for isolating the monoclonal antibody. In one embodiment, the mammal used for immunization is a mouse.

Examples of suitable carrier proteins include, but are not limited to, bovine serum albumin (BSA) and keyhole limpet hemocyanin (KLH).

Monoclonal antibodies of the invention can be used to detect the presence of one or more target nucleic acid molecules in a biological system, including, but not limited to, a tissue, a cell or a cell lysate. Detection of target nucleic acid molecules can be used, for example, to determine bioavailabilty of said target molecule. Examples of target nucleic acid molecules include, but are not limited to, nucleic acid molecules having SEQ ID NOS: 1, 3,16, or 17 and/or having at least one 2'-deoxy-2'-C-allyl Uridine nucleotide.

The invention also features mAb conjugates. The monoclonal antibodies of the present invention can be conjugated to a predetermined compound or molecule that is capable of interacting with the target nucleic acid molecule in the system and providing a detectable signal or response. Compounds and molecules known in the art that can be used in these applications include, but are not limited to, antibodies, labeled antibodies, allozymes, aptamers, labeled nucleic acid probes, molecular beacons, fluorescent molecules, radioisotopes, pofysaccharides, and other compounds capable of interacting with the target nucleic acid molecule and generating a detectable signal upon target interaction, and the like. Examples of such compounds are further described in U.S. Ser. No. 09/800,594, filed on Mar. 6, 2001 (now abandoned), which is incorporated herein by reference in its entirety.

In another embodiment, polyethylene glycol (PEG) can be covalently attached to the mAb compounds of the present invention. The attached PEG can be any molecular weight, preferably from about 2000 to about 50,000 daltons (Da).

In one embodiment, the invention features a method of detecting the presence of a nucleic acid molecule having a 2'-deoxy-2'-C-allyl Uridine nucleotide in a patient or subject, comprising: (a) Obtaining a sample from the patient or subject; and (b) Contacting the sample of (a) with a monoclonal antibody or monoclonal antibody conjugate of the invention under conditions suitable for detecting the presence of the nucleic acid molecule in the patient or subject.

In another embodiment, the invention features a method of detecting the presence of a nucleic acid molecule comprising a nucleoside and/or nucleotide having Formula I in a patient or subject, comprising: (a) Obtaining a sample from the patient or subject; and (b) Contacting the sample of (a) with a monoclonal antibody or monoclonal antibody conjugate of the invention under conditions suitable for detecting the presence of the nucleic acid molecule in the patient or subject.

In another embodiment, the invention features a method of detecting the presence of a nucleic acid molecule having SEQ ID NO: 1, 3, 16, or 17 in a patient or subject, comprising: (a) Obtaining a sample from the patient or subject; and (b) Contacting the sample of (a) with a monoclonal antibody or monoclonal antibody conjugate of the invention under conditions suitable for detecting the presence of the nucleic acid molecule in the patient or subject.

In one embodiment, the invention features a method for determining the level of a nucleic acid molecule in a mammal, comprising: (a) Administering the candidate nucleic acid molecule to the mammal; (b) Obtaining a sample from the mammal; (c) Contacting the sample of (b) with a monoclonal antibody or monoclonal antibody conjugate of the invention under conditions suitable for detecting the presence of the nucleic acid molecule in the sample, and (d) Assaying the level of the nucleic acid molecule in the sample under conditions suitable to determine the level of the nucleic acid molecule in the sample and/or mammal. In one embodiment, the mammal is non-human (e.g., including, but not limited to, a mouse, rat, rabbit, or pig). In yet another embodiment, the mammal is a human.

Examples of samples include, but are not limited to samples derived from cells and/or tissues, such as serum, blood, urine, and cell lysates.

The invention also features monoclonal antibodies and monoclonal antibody conjugates that direct the in vivo localization of target nucleic acid molecules. In one embodiment, the invention features a mAb that directs the in vivo localization of a target nucleic acid molecule. In another embodiment, the invention features a mAb conjugate that directs the in vivo localization of a target nucleic acid molecule. In one embodiment, the mAb conjugate comprises a mAb of the invention and one or more conjugated groups or moieties capable of directing the in vivo localization of a target nucleic acid molecule. Such conjugated groups or moieties can include proteins, peptides, polypeptides, receptor ligands, lipids, phospholipids, carbohydrates, polycations, polyethylene glycols, or other polymers or molecules, such as biologically active molecules that facilitate bioavailability or enable cell or tissue specific localization of pendant molecules described above. Interaction of the conjugated mAb with a nucleic acid molecule is expected to facilitate pharmacokinetics and the in vivo bioavailability of a nucleic acid molecule to a particular cell and/or tissue type of an organism, such as a patient or subject.

Another embodiment of the invention encompasses mAb conjugates comprising targeting components for increasing the transport of other impermeable and/or lipophilic compounds into cells. Targeting components can include ligands for cell surface receptors including, but not limited to, peptides and proteins, glycolipids, lipids, carbohydrates, and their synthetic variants, (e.g., including, but not limited to, ligands for asialoglycoprotein (ASGPr) receptors or folate receptors). Particular methods of generating conjugated antibodies are described in Thorpe et al., U.S. Pat. No. 6,342,221, incorporated by reference herein.

The compounds or conjugates and methods of the present invention are useful for introducing nucleotides, nucleosides, nucleic acid molecules, lipids, peptides, proteins, and/or non-nucleosidic small molecules into a cell. For example, the invention can be used for nucleotide, nucleoside, nucleic acid, lipids, peptides, proteins, and/or non-nucleosidic small molecule delivery where the corresponding target site of action exists intracellularly.

In one specific embodiment, the compounds of the present invention are conjugates of molecules that interact with ASGPr receptors, and also provide a number of features that allow the efficient delivery and subsequent release of conjugated compounds across biological membranes. The compounds utilize chemical linkages between galactose, galactosamine, or N-acetyl galactosamine substituents and the compound to be delivered which are of such length that they interact preferentially with ASGPr receptors. Furthermore, the chemical linkages between galactose, galactosamine, or N-acetyl galactosamine substituents and the compound to be delivered can be designed as degradable linkages, for example, by utilizing a phosphate linkage that is proximal to a nucleophile, such as a hydroxyl group, or utilizing a nucleic acid linker comprising ribonucleotides. Deprotonation of the hydroxyl group or an equivalent group, as a result of pH or interaction with a nuclease, can result in nucleophilic attack of the phosphate resulting in a cyclic phosphate intermediate that can then be hydrolyzed. This cleavage mechanism is analogous to RNA cleavage in the presence of a base or RNA nuclease. Alternately, other degradable linkages can be selected that respond to various factors such as UV irradiation (photolabile linker), cellular nucleases, pH, temperature etc. The use of degradable linkages allows the delivered compound to be released in a predetermined system, for example, in the cytoplasm of a cell, or in a particular cellular organelle. Non-limiting examples of such linkers are described in Vargeese et al., U.S. Ser. No. 60/311,865, incorporated by reference herein.

In another embodiment, polyethylene glycol (PEG) can be covalently attached to mAb compounds of the present invention. The attached PEG can be any molecular weight, preferably from about 2,000 to about 50,000 daltons (Da).

The monoclonal antibodies of the invention can be conjugated directly to the described compounds to form a mAb conjugate or can be conjugated via a linker, such as a linker described herein.

In one embodiment, a patient or subject contemplated by the invention is a patient or subject treated with a therapeutic nucleic acid molecule having a 2'-deoxy-2'-C-allyl Uridine nucleotide. Such a therapeutic nucleic acid molecule can include, but is not limited to, an enzymatic nucleic acid molecule, allozyme, antisense nucleic acid, 2-5A antisense chimera, triplex forming oligonucleotide, decoy RNA, dsRNA, siRNA, aptamer, and/or antisense nucleic acid comprising nucleic acid-cleaving chemical groups, which comprise a 2'-deoxy-2'-C-allyl Uridine nucleotide.

In one embodiment, a patient or subject contemplated by the invention is a patient or subject treated with a therapeutic nucleic acid molecule comprising a nucleoside and/or nucleotide having Formula I. Such a therapeutic nucleic acid molecule can include, but is not limited to, an enzymatic nucleic acid molecule, allozyme, antisense nucleic acid, 2-5A antisense chimera, triplex forming oligonucleotide, decoy RNA, dsRNA, siRNA, aptamer, and/or antisense nucleic acid comprising nucleic acid-cleaving chemical groups, which comprise a nucleoside and/or nucleotide having Formula I.

In one embodiment, a patient or subject contemplated by the invention is a patient or subject treated with a therapeutic nucleic acid molecule having SEQ ID NO: 1, 3, 16, or 17.

In one embodiment, the invention features a method for screening candidate nucleic acid molecules for bioavailability in a mammal, comprising: (a) Administering the candidate nucleic acid molecule to the mammal; (b) Obtaining a sample from the mammal, including, but not limited to, a blood sample or tissue sample; and (c) Contacting the sample of (b) with a monoclonal antibody or monoclonal antibody conjugate of the invention under conditions suitable for detecting the presence of the nucleic acid molecule in the sample. In one embodiment, the mammal is non-human (e.g., including, but not limited to, a mouse, rat, rabbit, or pig). In yet another embodiment, the mammal is a human.

The methods of the present invention can be used to determine the effect that various modifications to the structure of a nucleic acid molecule can have on bioavailability of the nucleic acid molecule. Such modifications include, but are not limited to, complete or partial chemical modification of a nucleic acid backbone, sugar, base, or any combination thereof, and/or conjugation of the nucleic acid molecule with various substituent groups or biologically active molecules that modulate the distribution, pharmacokinetics, pharmacodynamics, and/or bioavailability of the nucleic acid molecule. Non-limiting examples of such chemical modifications and conjugates are described in Vargeese et al., U.S. Ser. No. 60/311,865.

The compounds of the invention, including, but not limited to, monoclonal antibodies and conjugates thereof, can be administered directly to a patient or subject, can be added directly to cells or tissues isolated from a patient or subject, or can be complexed with cationic lipids, packaged within liposomes, or otherwise delivered to target cells or tissues. In one embodiment, the invention features a composition comprising a monoclonal antibody, monoclonal antibody conjugate or mAB compound thereof and a pharmaceutically acceptable carrier, for example, any of the carriers described for the compositions and formulations discussed herein.

The mAb compounds can be locally administered to relevant tissues ex vivo, or in vivo through injection or infusion pump, with or without their incorporation in biopolymers. The compounds of the instant invention, individually, or in combination or in conjunction with other drugs, can be used to treat various diseases or conditions such as cancer, including, but not limited to, breast, lung, prostate, colorectal, brain, esophageal, bladder, pancreatic, cervical, head and neck, and ovarian cancer, melanoma, lymphoma, glioma, multidrug resistant cancers, or viral infections including, but not limited to HIV, HBV, HCV, CMV, RSV, HSV, poliovirus, influenza, rhinovirus, west Nile virus, Ebola virus, foot and mouth virus, and papilloma virus infection. For example, to treat a disease or condition associated with the levels of a pathogenic protein, the patient can be treated, or other appropriate cells can be treated, as is evident to those skilled in the art, individually or in combination with one or more drugs under conditions suitable for the treatment.

In a further embodiment, the mAb, mAb conjugates and compositions thereof can be used in combination with other known treatments to treat conditions or diseases discussed above. For example, the mAb compounds of the present invention can be used in combination with one or more known therapeutic agents to treat breast, lung, prostate, colorectal, brain, esophageal, bladder, pancreatic, cervical, head and neck, and/or ovarian cancer, melanoma, lymphoma, glioma, multidrug resistant cancers, and/or HIV, HBV, HCV, CMV, RSV, HSV, poliovirus, influenza, rhinovirus, west Nile virus, Ebola virus, foot and mouth virus, and papilloma virus infection. The foregoing list is provided for illustrative purposes only and is not to be construed as limiting the invention in any way.

BRIEF DESCRIPTION OF THE DRAWINGS

FIG. 1 shows the chemical structure of a series of modified uridines used herein: (1) 5'-phosphateof 2'-deoxy-2'-C-allyl-uridine; (2): 2'-deoxy-2'-amino uridine; (3):2'-o-methyl uridine; (4): 2'-deoxy uridine; (5): 2'-O-allyl uridine; (6) : 2'-deoxy-2'-propyl uridine; (7): 2'-deoxy-2'-C-allyl cytidine.

DETAILED DESCRIPTION OF THE INVENTION

Figure 2:
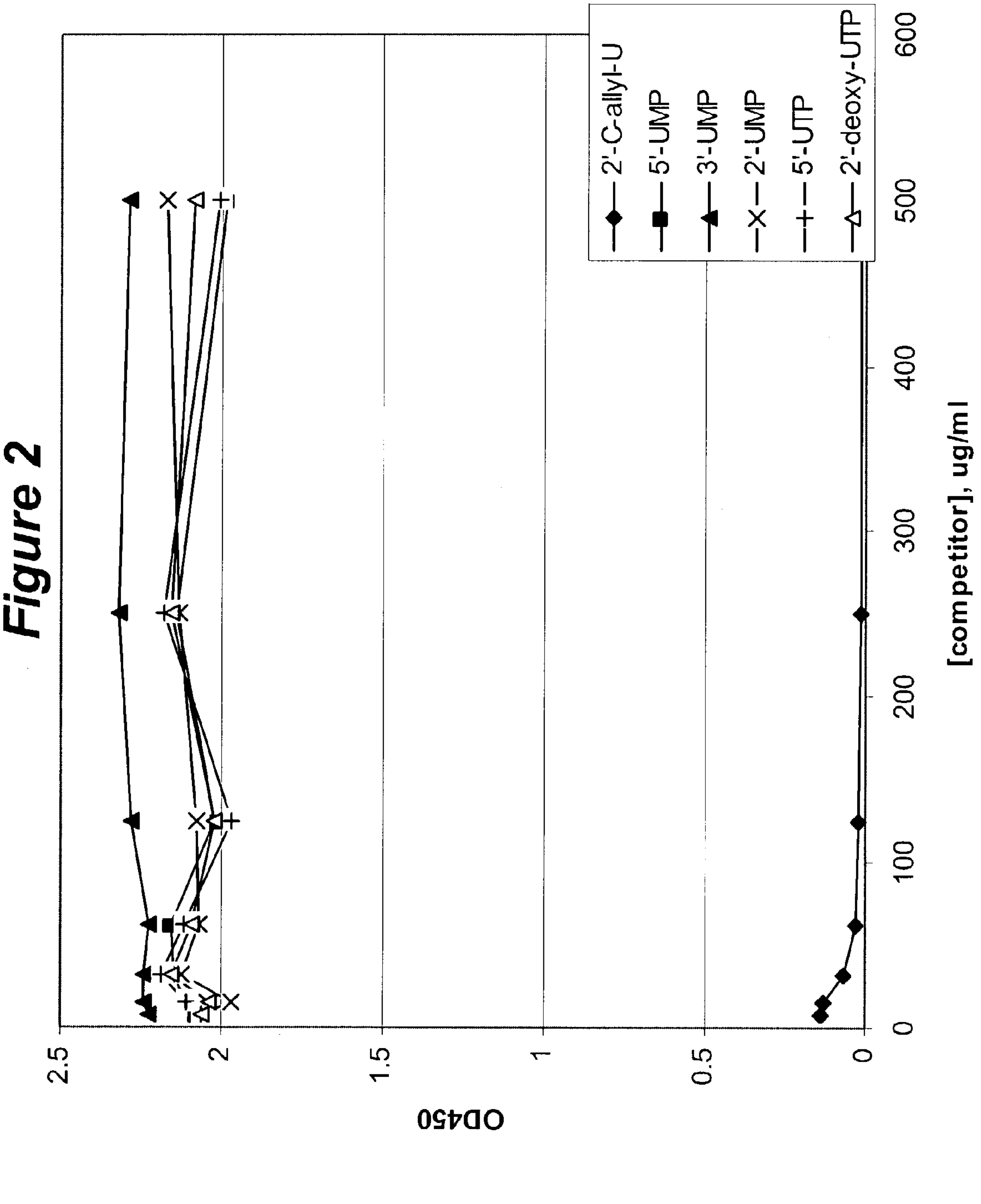
FIG. 2 shows the inhibition of binding of 1 μg/of CA1USR mAb by increasing concentrations of different nucleotide competitors. The change in binding by CA1USR to 2'-C-allyl U-KLH coupled to DNA-Bind plates with different concentrations of a series of nucleotide competitors in solution is shown. (♦); 2'-C-allyl U; (■): 5' UMP; (▲): 3' UMP; (×): 2' UMP; (+): 5' UTP; (Δ): 2' deoxy UTP, respectively, were incubated with 1 μg/ml of CA1USR prior to addition of the competitor-antibody mixture to 2'-deoxy-2'-C-allyl Uridine coupled to KLH.

The term "biodegradable nucleic acid linker molecule" as used herein, refers to a nucleic acid molecule that is designed as a biodegradable linker to connect one molecule to another molecule, for example, a biologically active molecule. The stability of the biodegradable nucleic acid linker molecule can be modulated by using various combinations of ribonucleotides, deoxyribonucleotides, and chemically modified nucleotides, for example 2'-O-methyl, 2'-fluoro, 2'-amino, 2'-O-amino, 2'-C-allyl, 2'-O-allyl, and other 2'-modified or base modified nucleotides. The biodegradable nucleic acid linker molecule can be a dimer, trimer, tetramer or longer nucleic acid molecule, for example, an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus based linkage, for example, a phosphoramidate or phosphodiester linkage. The biodegradable nucleic acid linker molecule can also comprise nucleic acid backbone, nucleic acid sugar, or nucleic acid base modifications.

The term "biodegradable" as used herein, refers to degradation in a biological system, for example, enzymatic degradation or chemical degradation.

The term "biologically active molecule" as used herein, refers to compounds or molecules that are capable of eliciting or modifying a biological response in a system. Non-limiting examples of biologically active molecules contemplated by the instant invention include therapeutically active molecules such as antibodies, hormones, antivirals, peptides, proteins, chemotherapeutics, small molecules, vitamins, co-factors, nucleosides, nucleotides, oligonucleotides, enzymatic nucleic acids, antisense nucleic acids, triplex forming oligonucleotides, 2,5-A chimeras, siRNA, dsRNA, allozymes, aptamers, decoys and analogs thereof. Biologically active molecules of the invention can also include molecules capable of modulating the pharmacokinetics and/or pharmacodynamics of other biologically active molecules, for example, lipids and polymers such as polyamines, polyamides, polyethylene glycol and other polyethers.

The term "phospholipid" as used herein, refers to a hydrophobic molecule comprising at least one phosphorus group. For example, a phospholipid can comprise a phosphorus containing group and saturated or unsaturated alkyl group, optionally substituted with OH, COOH, oxo, amine, or substituted or unsubstituted aryl groups.

The term "enzymatic nucleic acid molecule" as used herein refers to a nucleic acid molecule which has complementarity in a substrate binding region to a specified gene target, and also has an enzymatic activity which is active to specifically cleave target RNA. That is, the enzymatic nucleic acid molecule is able to intermolecularly cleave RNA and thereby inactivate a target RNA molecule. These complementary regions allow sufficient hybridization of the enzymatic nucleic acid molecule to the target RNA and thus permit cleavage. One hundred percent complementarity is preferred, but complementarity as low as 50–75% can also be useful in this invention (see for example Werner and Uhlenbeck, 1995, Nucleic Acids Research, 23, 2092–2096; Hammann et al., 1999, Antisense and Nucleic Acid Drug Dev., 9, 25–31). The nucleic acids can be modified at the base, sugar, and/or phosphate groups. The term enzymatic nucleic acid is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terms describe nucleic acid molecules with enzymatic activity. The specific enzymatic nucleic acid molecules described in the instant application are not limiting of the invention and those skilled in the art will recognize that what is most important in an enzymatic nucleic acid molecule of this invention is that it has a specific substrate binding site which is complementary to one or more of the target nucleic acid regions, and that it has nucleotide sequences within or surrounding that substrate binding site which impart a nucleic acid cleaving and/or ligation activity to the molecule (Cech et al., U.S. Pat. No. 4,987,071; Cech et al., 1988, 260 JAMA 3030).

The term "nucleic acid molecule" as used herein, refers to a molecule having nucleotides. The nucleic acid can be single, double, or multiple stranded and can comprise modified or unmodified nucleotides or non-nucleotides or various mixtures and combinations thereof.

Figure 6:
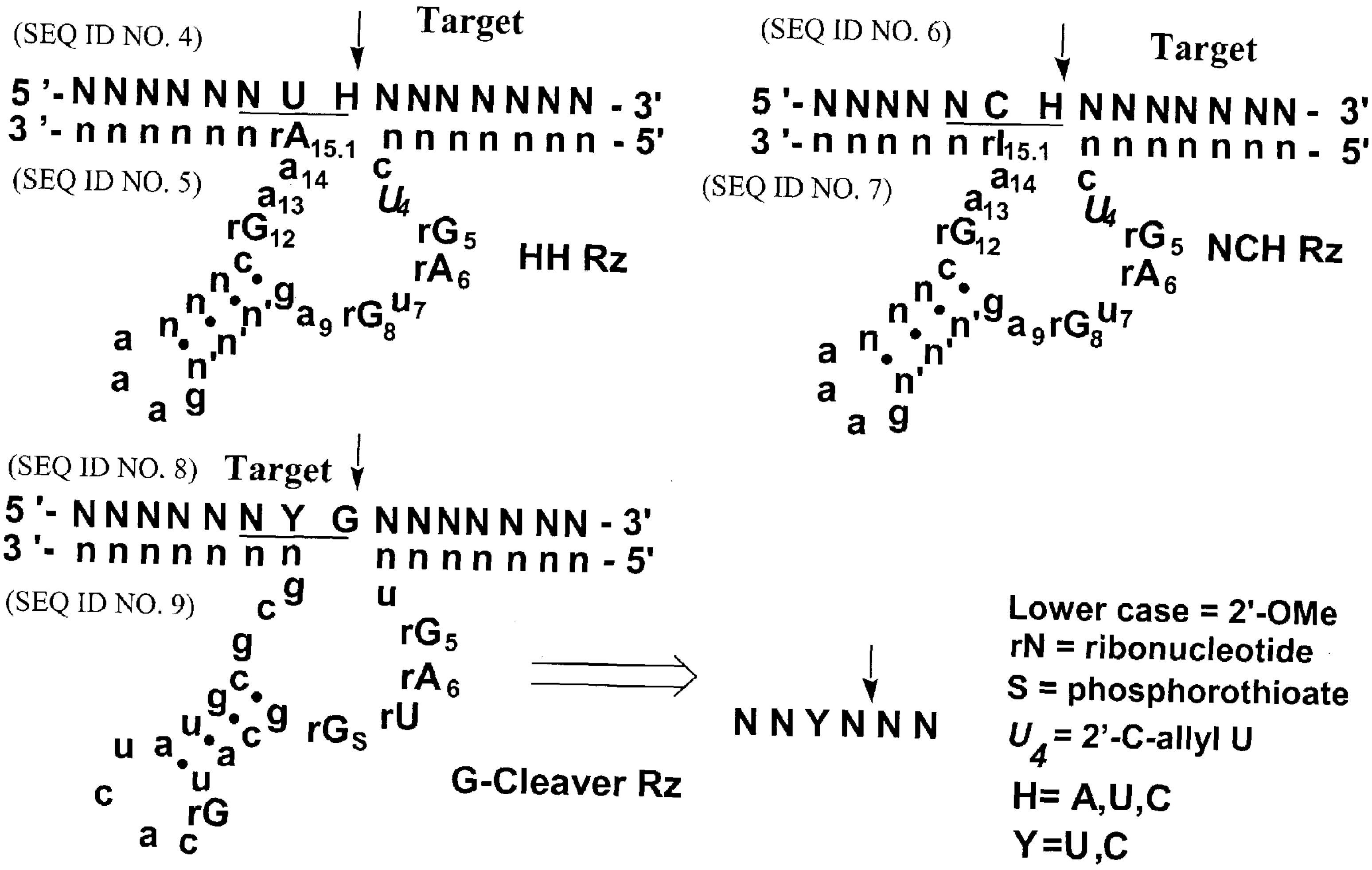
FIG. 6 shows examples of chemically stabilized ribozyme motifs. HH Rz, represents hammerhead ribozyme motif (Usman et at., 1996, Curr. Op. Struct. Bio., 1, 527); NCH Rz represents the NCH ribozyme motif (Ludwig et at., International PCT Publication No. WO 98/58058 and U.S. patent application Ser. No. 08/878,640, now abandoned); G-Cleaver, represents G-cleaver ribozyme motif (Kore et at., 1998, Nucleic Acids Research 26, 4116–4120, Eckstein et al., U.S. Pat. No. 6,127,173). N or n, represent independently a nucleotide which can be either the same or different and have complementarity to each other; rI, represents ribo-Inosine nucleotide; arrow indicates the site of cleavage within the target. Position 4 of the HH Rz and the NCH Rz is shown as having 2'-C-allyl modification, but those skilled in the art will recognize that this position can be modified with other modifications well known in the art, so long as such modifications do not significantly inhibit the activity of the ribozyme.

The term "Inozyme" or "NCH" as used herein refers to an enzymatic nucleic acid molecule comprising a motif as is generally shown as NCH Rz in FIG. 6 and described in Ludwig et al., International PCT Publication No. WO 98/58058 and U.S. patent application Ser. No. 08/878,640 (now abandoned) herein incorporated by reference in its entirety. Inozymes possess endonuclease activity to cleave nucleic acid substrates having a cleavage triplet NCH/, where N is a nucleotide, C is cytidine and H is adenosine, uridine or cytidine, and/represents the cleavage site. H is used interchangeably with X. Inozymes can also possess endonuclease activity to cleave nucleic acid substrates having a cleavage triplet NCN/, where N is a nucleotide, C is cytidine, and/represents the cleavage site. "I" in FIG. 6 represents an Inosine nucleotide, preferably a ribo-Inosine or xylo-Inosine nucleoside.

The term "G-cleaver" as used herein refers to an enzymatic nucleic acid molecule comprising a motif as generally shown as G-cleaver Rz in FIG. 6 and described in Eckstein et al., U.S. Pat. No. 6,127,173, herein incorporated by reference in its entirety. G-cleavers possess endonuclease activity to cleave nucleic acid substrates having a cleavage triplet NYN/, where N is a nucleotide, Y is uridine or cytidine and/represents the cleavage site. G-cleavers can be chemically modified as generally shown in FIG. 6.

Figure 7:
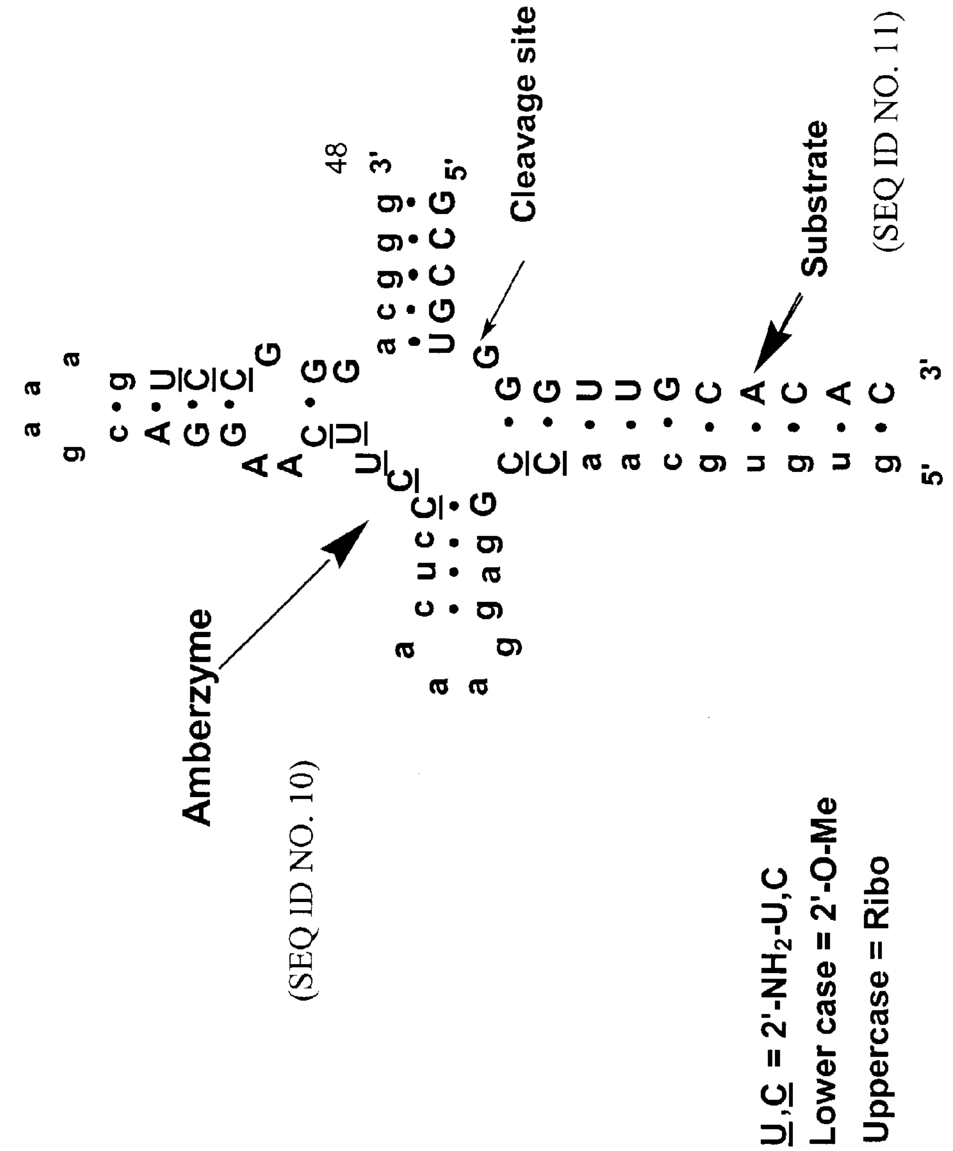
FIG. 7 shows an example of an Amberzyme ribozyme motif that is chemically stabilized (see for example Beigelman et at., International PCT publication No. WO 99/55857 and U.S. patent application Ser. No. 09/476,387, now U.S. Pat. No. 6,617,438).

The term "amberzyme" as used herein refers to an enzymatic nucleic acid molecule comprising a motif as generally shown in FIG. 7 and described in Beigelman et al., International PCT publication No. WO 99/55857 and U.S. patent application Ser. No. 09/476,387 (now U.S. Pat. No. 6,617, 438), herein incorporated by reference in its entirety. Amberzymes possess endonuclease activity to cleave nucleic acid substrates having a cleavage site. Amberzymes can be chemimally modified to increase nuclease stability through substitutions as generally shown in FIG. 7. In addition, differing nucleoside and/or non-nucleoside linkers can be used to substitute the 5'-gaaa-3' loops shown in the figure. Amberzymes represent a non-limiting example of an enzymatic nucleic acid molecule that does not require a ribonucleotide (2'-OH) group within its own nucleic acid sequence for activity.

Figure 8:
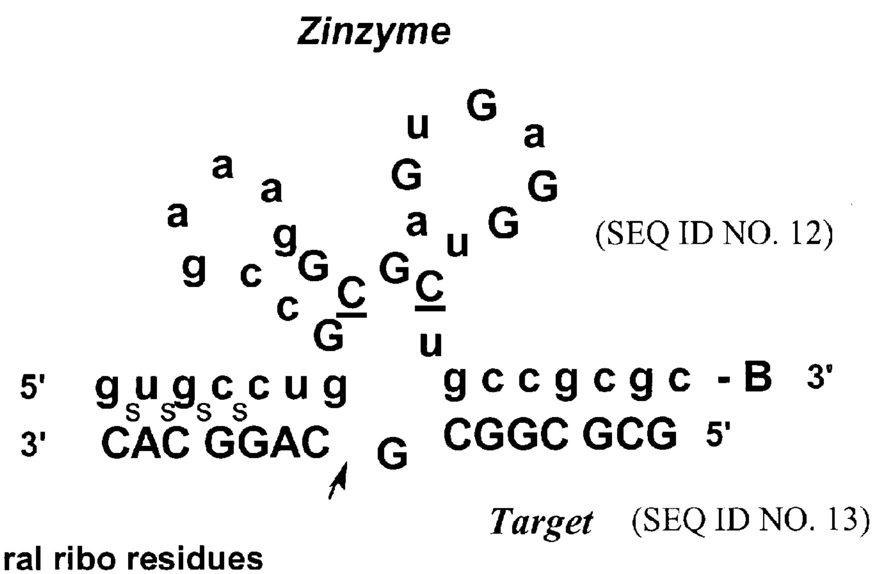
FIG. 8 shows an example of a Zinzyme A ribozyme motif that is chemically stabilized (see for example Beigelman et al., International PCT publication No. WO 99/55857 and U.S. patent application Ser. No. 09/918,728, now abandoned).

The term "zinzyme" as used herein refers to an enzymatic nucleic acid molecule comprising a motif as generally shown in FIG. 8 and described in Beigelman et al., International PCT publication No. WO 99/55857 and U.S. patent application Ser. No. 09/918,728, herein incorporated by reference in its entirety. Zinzymes possess endonuclease activity to cleave nucleic acid substrates having a cleavage triplet including, but not limited to, YG/Y, where Y is uridine or cytidine, and G is guanosine and/represents the cleavage site. Zinzymes can be chemically modified to increase nuclease stability through substitutions as generally shown in FIG. 8, including substituting 2'-O-methyl guanosine nucleotides for guanosine nucleotides. In addition, differing nucleotide and/or non-nucleotide linkers can be used to substitute the 5'-gaaa-2' loop shown in the figure. Zinzymes represent a non-limiting example of an enzymatic nucleic acid molecule that does not require a ribonucleotide (2'-OH) group within its own nucleic acid sequence for activity.

Figure 9:
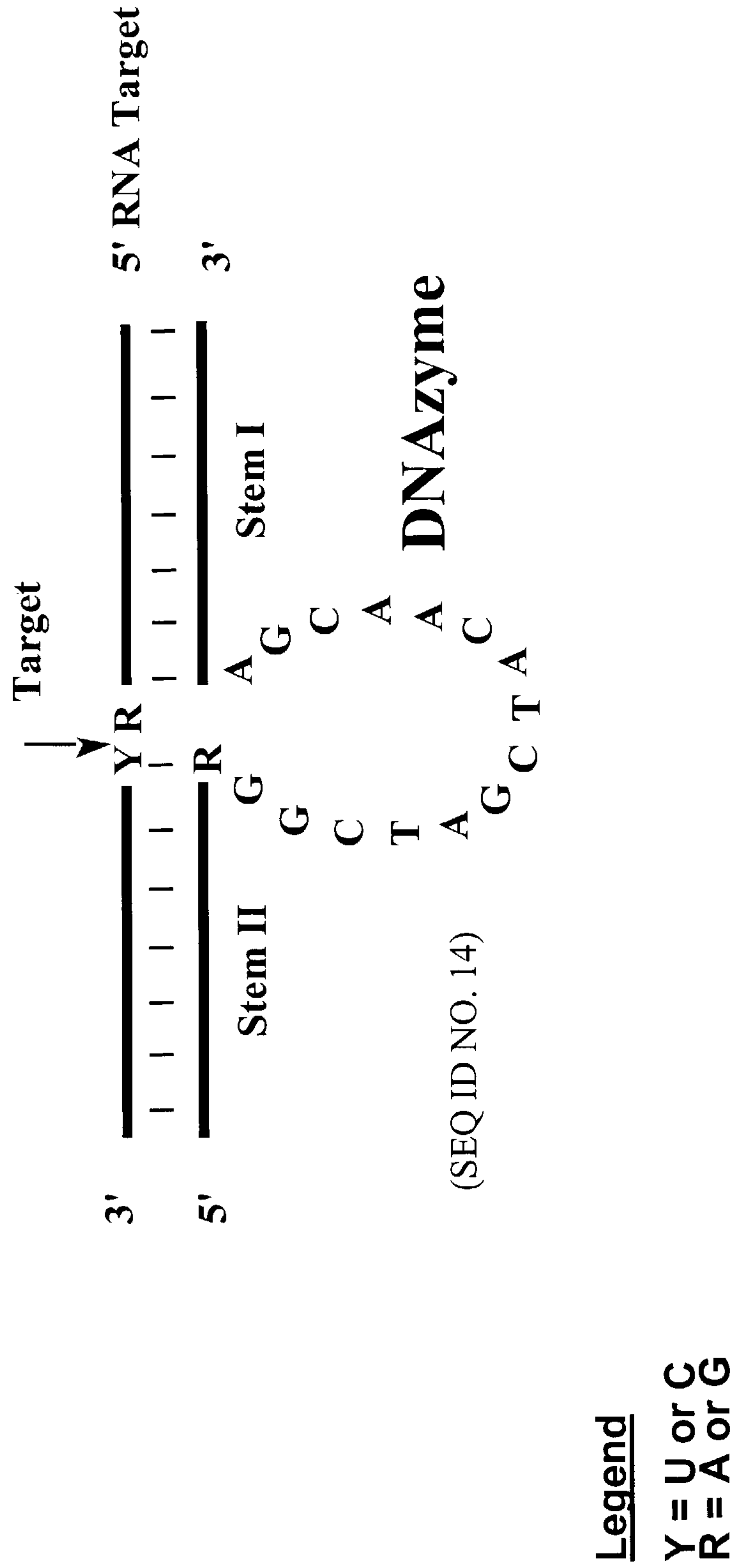
FIG. 9 shows an example of a DNAzyme motif described by Santoro et al., 1997, PNAS, 94, 4262 and Joyce et al., U.S. Pat. No. 5,807,718.
Figure 10:
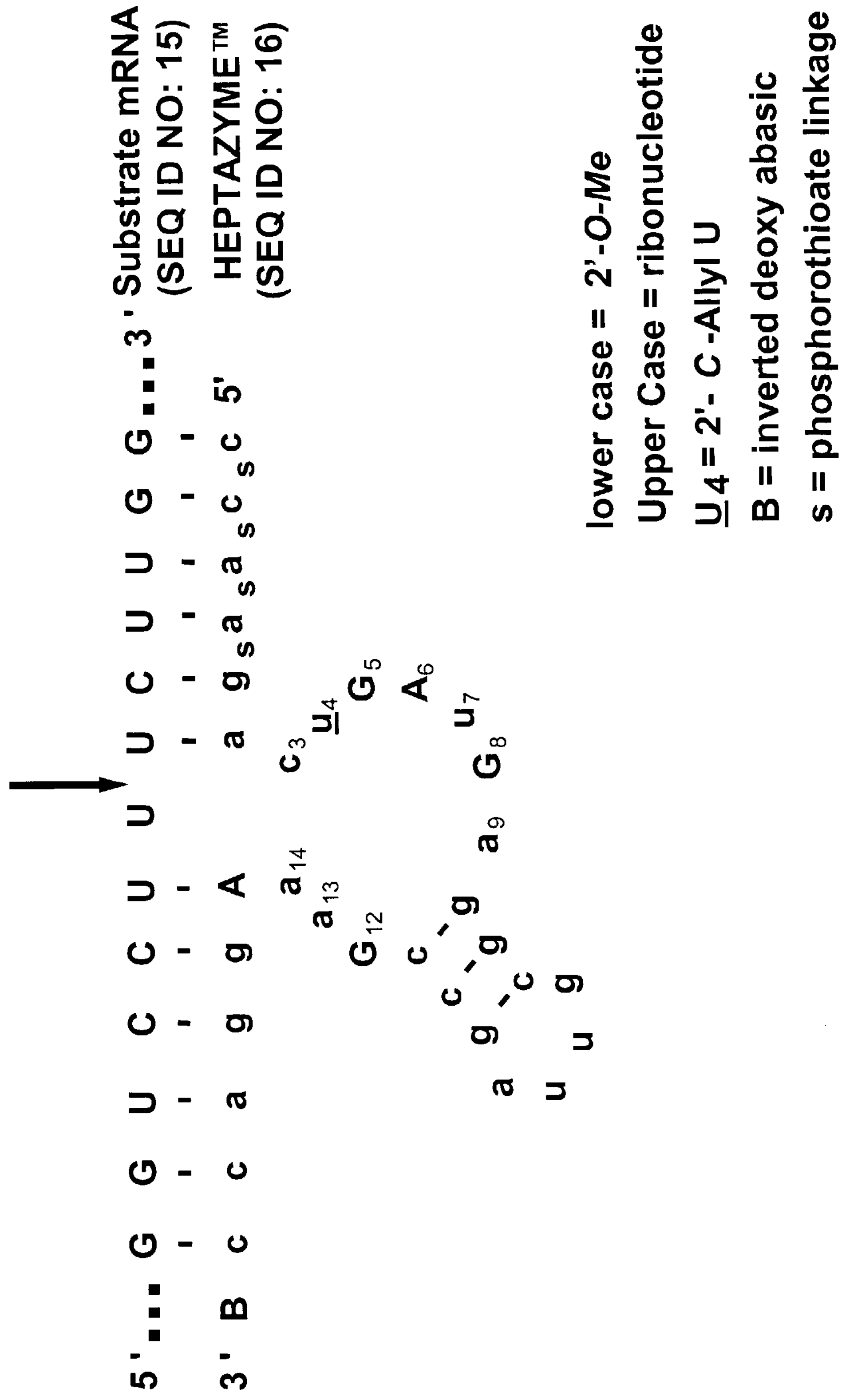
FIG. 10 shows the chemical structure of a HEPTAZYME™ enzymatic nucleic acid (SEQ ID NO: 16).
Figure 11:
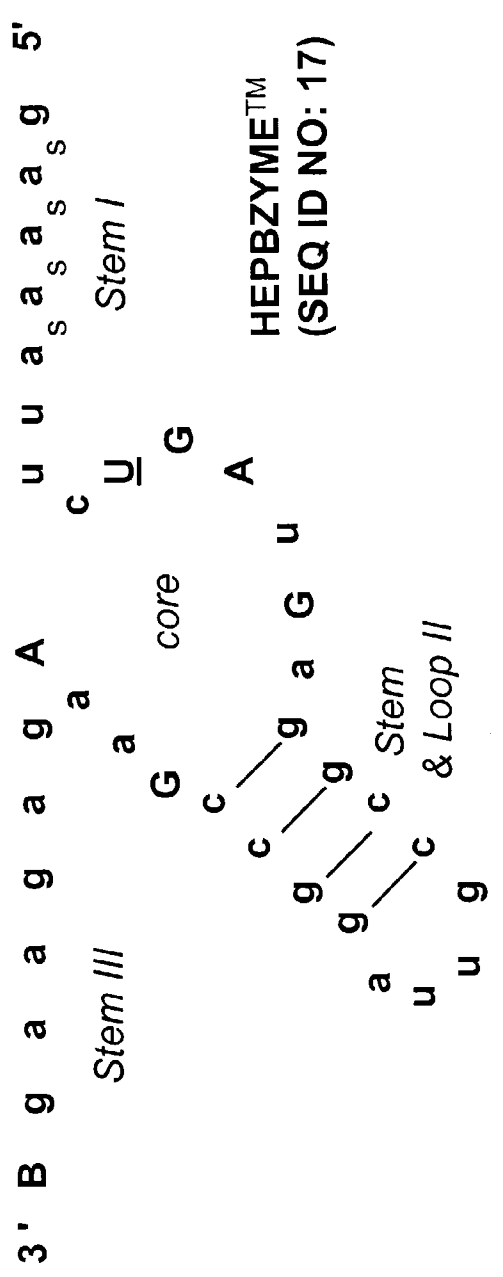
FIG. 11 shows the chemical structure of a HEPBZYME™ enzymatic nucleic acid (SEQ ID NO: 17).

The term 'DNAzyme' as used herein refers to an enzymatic nucleic acid molecule that does not require the presence of a 2'-OH group within its own nucleic acid sequence for activity. In particular embodiments, the enzymatic nucleic acid molecule can have an attached linker or linkers or other attached or associated groups, moieties, or chains containing one or more nucleotides with 2'-OH groups. DNAzymes can be synthesized chemically or expressed endogenously in vivo, by means of a single stranded DNA vector or equivalent thereof. An example of a DNAzyme is shown in FIG. 9 and is generally reviewed in Usman et al., U.S. Pat. No. 6,159,714, herein incorporated by reference in its entirety; Chartrand et al., 1995, NAR 23, 4092; Breaker et al., 1995, Chem. Bio. 2, 655; Santoro et al., 1997, PNAS 94, 4262; Breaker, 1999, Nature Biotechnology, 17, 422–423; and Santoro et. al., 2000, J. Am. Chem. Soc., 122, 2433–39. The "10–23" DNAzyme motif is one particular type of DNAzyme that was evolved using in vitro selection, see Santoro et al., supra and as generally described in Joyce et al., U.S. Pat. No. 5,807,718, herein incorporated by reference in its entirety. Additional DNAzyme motifs can be selected for using techniques similar to those described in these references, and hence, are within the scope of the present invention.

The term "antisense nucleic acid", as used herein refers to a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review, see Stein and Cheng, 1993 Science 261, 1004 and Woolf et al., U.S. Pat. No. 5,849,902). Typically, antisense molecules are complementary to a target sequence along a single contiguous sequence of the antisense molecule. However, in certain embodiments, an antisense molecule can bind to a substrate such that the substrate molecule forms a loop, and/or an antisense molecule can bind such that the antisense molecule forms a loop. Thus, the antisense molecule can be complementary to two or more non-contiguous substrate sequences or two (or more) non-contiguous sequence portions of an antisense molecule can be complementary to a target sequence or both. For a review of current antisense strategies, see Schmajuk et al., 1999, J. Biol. Chem., 274, 21783–21789, Delihas et al., 1997, Nature, 15, 751–753, Stein et al., 1997, Antisense N. A. Drug Dev., 7, 151, Crooke, 2000, Methods Enzymol., 313, 3–45; Crooke, 1998, Biotech. Genet. Eng. Rev., 15, 121–157, Crooke, 1997, Ad. Pharmacol., 40, 1–49. In addition, antisense DNA can be used to target RNA by means of DNA-RNA interactions, thereby activating RNase H, which digests the target RNA in the duplex. The antisense oligonucleotides can comprise one or more RNAse H activating regions, which are capable of activating RNAse H cleavage of a target RNA. Antisense DNA can be synthesized chemically or expressed via the use of a single stranded DNA expression vector or equivalent thereof.

The term "RNase H activating region" as used herein refers to a region (generally greater than or equal to about 4 nucleotides to about 25 nucleotides in length, preferably from about 5 nucleotides to about 11 nucleotides in length) of a nucleic acid molecule capable of binding to a target RNA to form a non-covalent complex that is recognized by a cellular RNase H enzyme (see for example Arrow et al., U.S. Pat. No. 5,849,902; Arrow et al., U.S. Pat. No. 5,989, 912). The RNase H enzyme binds to the nucleic acid molecule-target RNA complex and cleaves the target RNA sequence. The RNase H activating region comprises, for example, phosphodiester, phosphorothioate (preferably at least four of the nucleotides are phosphorothioate substitutions; more specifically, 4–11 of the nucleotides are phosphorothioate substitutions); phosphorodithioate, 5'-thiophosphate, or methylphosphonate backbone chemistry or a combination thereof. In addition to one or more backbone chemistries described above, the RNase H activating region can also comprise a variety of sugar chemistries. For example, the RNase H activating region can comprise deoxyribose, arabino, fluoroarabino or a combination thereof, nucleotide sugar chemistry. Those skilled in the art will recognize that the foregoing are non-limiting examples and that any combination of phosphate, sugar and base chemistry of a nucleic acid that supports the activity of RNase H enzyme is within the scope of the definition of the RNase H activating region and the instant invention.

The term "2–5A chimera" as used herein refers to an oligonucleotide containing a 5'-phosphorylated 2'-5'-linked adenylate residue. These chimeras bind to target RNA in a sequence-specific manner and activate a cellular 2–5A-dependent ribonuclease which, in turn, cleaves the target RNA (Torrence et al., 1993 Proc. Natl. Acad. Sci. USA 90, 1300; Silverman et al., 2000, Methods Enzymol., 313, 522–533; Player and Torrence, 1998, Pharmacol. Ther., 78, 55–113).

The term "gene" it as used herein refers to a nucleic acid that encodes an RNA, for example, nucleic acid sequences including, but not limited to, structural genes encoding a polypeptide.

The term "pathogenic protein" as used herein refers to one or more endogenous or exongenous proteins that are associated with a disease state or condition, for example a particular cancer or viral infection.

The term "complementarity" as used herein refers to the ability of a nucleic acid to form hydrogen bond(s) with another RNA sequence by either traditional Watson-Crick base pairing or other non-traditional types. In reference to the nucleic molecules of the present invention, the binding free energy for a nucleic acid molecule with its target or complementary sequence is sufficient to allow the relevant function of the nucleic acid to proceed, e.g., enzymatic nucleic acid cleavage, antisense or triple helix inhibition. Determination of binding free energies for nucleic acid molecules is well known in the art (see, e.g., Turner et al., 1987, CSH Symp. Quant. Biol. LII pp.123–133; Frier et al., 1986, Proc. Nat. Acad. Sci. USA 83:9373–9377; Turner et al., 1987, J. Am. Chem. Soc. 109:3783–3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a first nucleic acid sequence will hydrogen bond with the same number of contiguous residues in a second nucleic acid sequence.

The term "RNA" as used herein refers to a molecule comprising at least one ribonucleotide residue. By "ribonucleotide" or "2'-OH" is meant a nucleotide with a hydroxyl group at the 2' position of a β-D-ribo-furanose moiety.

The term "decoy" as used herein refers to a nucleic acid molecule or aptamer that is designed to preferentially bind to a predetermined ligand. Such binding can result in the inhibition or activation of a target molecule. The decoy or aptamer can compete with a naturally occurring binding target for the binding of a specific ligand. For example, it has been shown that over-expression of HIV trans-activation response (TAR) RNA acts as a "decoy," which efficiently binds HIV tat protein, thereby preventing it from binding to TAR sequences present in the HIV RNA (Sullenger et al., 1990, Cell, 63, 601–608). This is but a single example and those in the art will recognize that other embodiments can be readily generated using techniques generally known in the art, see for example Gold et al., 1995, Annu. Rev. Biochem., 64, 763; Brody and Gold, 2000, J. Biotechnol., 74, 5; Sun, 2000, Curr. Opin. Mol. Ther., 2, 100; Kusser, 2000, J. Biotechnol., 74, 27; Hermann and Patel, 2000, Science, 287, 820; and Jayasena, 1999, Clinical Chemistry, 45, 1628. Similarly, a decoy RNA can be designed to bind to a receptor and block the binding of an effector molecule or a decoy RNA can be designed to bind to receptor of interest and prevent interaction with the receptor.

The term "single stranded RNA" (ssRNA) as used herein refers to a naturally occurring or synthetic ribonucleic acid molecule comprising a linear single strand, for example, a messenger RNA (mRNA), transfer RNA (tRNA), or ribosomal RNA (rRNA).

The term "single stranded DNA" (ssDNA) as used herein refers to a naturally occurring or synthetic deoxyribonucleic acid molecule comprising a linear single strand, for example, a sense or antisense gene sequence or EST (Expressed Sequence Tag).

The term "double stranded RNA" or "dsRNA" as used herein refers to a double stranded RNA molecule capable of RNA interference, including short interfering RNA (siRNA), see for example Bass, 2001, Nature, 411, 428–429; Elbashir et al., 2001, Nature, 411, 494–498).

The term "allozyme" as used herein refers to an allosteric enzymatic nucleic acid molecule, see for example George et al., U.S. Pat. Nos. 5,834,186 and 5,741,679, Shih et al., U.S. Pat. No. 5,589,332, Nathan et al., U.S. Pat. No. 5,871,914, all of which are herein incorporated by reference in their entireties; Nathan and Ellington, International PCT publication No. WO 00/24931, Breaker et al., International PCT Publication Nos. WO 00/26226 and 98/27104, and Sullenger et al., International PCT publication No. WO 99/29842. The term "2–5A chimera" as used herein refers to an oligonucleotide containing a 5'-phosphorylated 2'-5'-linked adenylate residue. These chimeras bind to target RNA in a sequence-specific manner and activate a cellular 2-5A-dependent ribonuclease which, in turn, cleaves the target RNA (see for example Torrence et al., 1993 Proc. Natl. Acad. Sci. USA 90, 1300; Silverman et al., 2000, Methods Enzymol., 313, 522–533; Player and Torrence, 1998, Pharmacol. Ther., 78, 55–113).

The term "triplex forming oligonucleotides" as used herein refers to an oligonucleotide that binds to a double-stranded DNA in a sequence-specific manner to form a triple-strand helix. Formation of such triple helix structure has been shown to inhibit transcription of the targeted gene (see for example Duval-Valentin et al., 1992 Proc. Natl. Acad. Sci. USA 89, 504; Fox, 2000, Curr. Med. Chem., 7, 17–37; Praseuth et. al., 2000, Biochim. Biophys. Acta, 1489, 181–206).

The term "cell" as used herein refers to its usual biological sense, and does not refer to an entire multicellular organism. A cell can be in vitro, e.g., in cell culture, or present in a multicellular organism, including, e.g., birds, plants and mammals such as humans, cows, sheep, apes, monkeys, swine, dogs, and cats. A cell can be prokaryotic (e.g., a bacterial cell) or eukaryotic (e.g., a mammalian or plant cell).

The term "non-nucleotide" as used herein refers to any group or compound which can be incorporated into a nucleic acid chain in place of one or more nucleotide units, including either sugar and/or phosphate substitutions, allowing the remaining bases to exhibit their enzymatic activity. The group or compound is abasic in that it does not contain a commonly recognized nucleotide base, such as adenosine, guanine, cytosine, uracil or thymine.

The term "nucleotide" as used herein, refers to a heterocyclic nitrogenous base in N-glycosidic linkage with a phosphorylated sugar. Nucleotides are recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and the like (see for example, Usman et al., U.S. Pat. No. 5,767,263; Eckstein et al., U.S. Pat. No. 5,672,695; Usman et al., U.S. Pat. No. 6,140,491; all hereby incorporated herein by reference). There are several examples of modified nucleic acid bases known in the art as summarized by Limbach et al., 1994, Nucleic Acids Res. 22, 2183. Some non-limiting examples of chemically modified and other natural nucleic acid bases that can be introduced into nucleic acids include, for example, inosine, purine, pyridin-4-one, pyridin-2-one, phenyl, pseudouracil, 2, 4, 6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g., 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid, 2-thiocytidine, threonine derivatives and the like (see for example Burgin et al., 1996, Biochemistry, 35, 14090; Uhlman & Peyman, supra). By "modified bases" in this aspect is meant nucleotide bases other than adenine, guanine, cytosine and uracil at 1' position or their equivalents; such bases can be used at any position, for example, within the catalytic core of an enzymatic nucleic acid molecule and/or in the substrate-binding regions of the nucleic acid molecule.

The term "nucleoside" as used herein refers to a heterocyclic nitrogenous base in N-glycosidic linkage with a sugar. Nucleosides are recognized in the art to include natural bases (standard), and modified bases well known in the art. Such bases are generally located at the 1' position of a nucleoside sugar moiety. Nucleosides generally comprise a base and sugar group. The nucleosides can be unmodified or modified at the sugar, and/or base moiety, (also referred to interchangeably as nucleoside analogs, modified nucleosides, non-natural nucleosides, non-standard nucleosides and the like (see for example, Usman et al., U.S. Pat. No. 5,767,263; Eckstein et al., U.S. Pat. No. 5,672,695; Usman et al., U.S. Pat. No. 6,140,491;; all hereby incorporated herein by reference in their entirety). There are several examples of modified nucleic acid bases known in the art as summarized by Limbach et al., 1994, Nucleic Acids Res. 22, 2183. Some non-limiting examples of chemically modified and other natural nucleic acid bases that can be introduced into nucleic acids include, inosine, purine, pyridin-4-one, pyridin-2-one, phenyl, pseudouracil, 2, 4, 6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g., 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid, 2-thiocytidine, threonine derivatives and the like (see for example Burgin et al., 1996, Biochemistry, 35, 14090; Uhlman & Peyman, supra). By "modified bases" in this aspect is meant nucleoside bases other than adenine, guanine, cytosine and uracil at 1' position or their equivalents; such bases can be used at any position, for example, within the catalytic core of an enzymatic nucleic acid molecule and/or in the substrate-binding regions of the nucleic acid molecule.

The term "cap structure" as used herein, refers to chemical modifications, which have been incorporated at either terminus of the oligonucleotide (see for example Wincott et al., WO 97/26270, incorporated herein by reference in its entirety ). These terminal modifications protect the nucleic acid molecule from exonuclease degradation, and help in delivery and/or localization within a cell. The cap can be present at the 5'-terminus (5'-cap) or at the 3'-terminus (3'-cap) or can be present on both termini. In non-limiting examples, the 5'-cap includes inverted abasic residue (moiety), 4', 5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270, incorporated herein by reference in its entirety).

The term "abasic" as used herein refers to sugar moieties lacking a base or having other chemical groups in place of a base at the 1' position, for example a 3',3'-linked or 5',5'-linked deoxyabasic ribose derivative (for more details see Adamic et al., U.S. Pat. No. 5,998,203, incorporated herein by reference in its entirety).

The term "unmodified nucleoside" as used herein refers to one of the bases adenine, cytosine, guanine, thymine, uracil joined to the 1' carbon of β-D-ribo-furanose.

The term "modified nucleoside" as used herein refers to any nucleotide base which contains a modification in the chemical structure of an unmodified nucleotide base, sugar and/or phosphate.

The term "carrier protein" as used herein, refers to any protein that is used as a scaffold for introducing an antigen during immunization. Non-limiting examples of carrier proteins include bovine serum albumin (BSA) or keyhole limpet hemocyanin.

The term "patient" or "subject" as used herein, refers to an organism, which is a donor or recipient of explanted cells or the cells themselves. "Patient" or "subject" also refers to an organism to which the nucleic acid molecules of the invention can be administered. Preferably, a patient or subject is a mammal or mammalian cells. More preferably, a patient or subject is a human or human cells.

The term "SJL mouse" as used herein refers to a mouse designated S (Swiss Webster) J(Jackson Labs) L (Lambert) or an equivalent strain of mouse highly susceptible to autoimmune disorders and suitable for raising antibodies.

The term "immunizing" as used herein refers to the process of administering an antigen to a suitable mammal for the purpose of generating antibodies to the antigen.

The term "fusion screen" or "fusion screening assay" as used herein refers to a method of screening for antibodies generated from a hybridoma fusion, or screening of antibodies generated via fusion of a lymphocyte or splenocyte to a myeloma, for example ELISA assay.

The term "hybridoma" as used herein refers to a cell that is created by fusing two cells, a secreting cell from the immune system, such as a B-cell, and an immortal cell, such as a myeloma, within a single membrane. The resulting hybrid cell can be cloned, producing identical daughter cells. Each of these daughter clones can secrete cellular products of the immune cell over several generations.

The term "immortal cell" refers to a cell or cell line that can be passaged in cell culture for several generations or indefinitely.

The term "coupling" as used herein refers to a reaction, either chemical or enzymatic, in which one atom, moiety, group, compound or molecule is joined to another atom, moiety, group, compound or molecule.

The term "linker molecule" as used herein refers to any diradical molecule that can connect one portion or component of a compound to another portion or component of the compound. Linkers can be of varying molecular weight, chemical composition, and/or length.

The term "degradable linker" or "cleavable linker" as used herein refers to linker moieties that are capable of cleavage under various conditions. Conditions suitable for cleavage include, but are not limited to, pH, UV irradiation, enzymatic activity, temperature, hydrolysis, elimination and substitution reactions, thermodynamic properties of the linkage, and the like.

The term "degradable nucleic acid linker" as used herein refers to degradable linkers comprising nucleic acids or oligonucleotides that are susceptible to chemical or enzymatic degradation, for example an oligoribonucleotide. The specific degree of degradability of the linker can be modulated by combining chemically modified nucleotides with naturally occurring nucleotides or by varying the number of pyrimidine nucleotides to purine nucleotides.

The term "photolabile linker" as used herein refers to linker moieties known in the art that are selectively cleaved under particular UV wavelengths. Compounds of the invention containing photolabile linkers can be used to deliver compounds to a target cell or tissue of interest and can be subsequently released in the presence of a UV source.

The term "nucleic acid conjugates" as used herein refers to nucleoside, nucleotide and oligonucleotide conjugates.

The term "monoclonal antibody conjugate" as used herein refers to any conjugate molecule comprising a monoclonal antibody coupled to another molecule, such as an nucleic acid molecule, polynucleotide, oligonucleotide, amino acid, peptide, polypeptide, lipid, phospholipid, or small molecule etc.

The term "lipid aggregate" as used herein refers to a lipid-containing composition, wherein the lipid is in the form of a liposome, micelle (non-lamellar phase) or other aggregates with one or more lipids.

The term "biological system" as used herein can be a eukaryotic system or a prokaryotic system, can be comprised of one or more bacterial cells, plant cells or mammalian cells, and extracts or lysates thereof. The system can be of plant origin, mammalian origin, yeast origin, Drosophila origin, or archebacterial origin.

The term "systemic administration" as used herein refers to the in vivo systemic absorption or accumulation of drugs in a blood stream followed by distribution throughout an entire body of an organism. Administration routes which lead to systemic absorption include, without limitation: intravenous, subcutaneous, intraperitoneal, inhalation, oral, intrapulmonary and intramuscular. Each of these administration routes expose the desired negatively charged polymers, e.g., nucleic acids, to an accessible diseased tissue. The rate of entry of a drug into the circulation has been shown to be a function of molecular weight or size. The use of a liposome or other drug carrier comprising the compounds of the present invention can potentially localize the drug, for example, in certain tissue types, such as the tissues of the reticular endothelial system (RES). A liposome formulation which can facilitate the association of a drug with the surface of cells, such as, lymphocytes and macrophages is also useful. This approach can provide enhanced delivery of the drug to target cells by taking advantage of the specificity of macrophage and lymphocyte immune recognition of abnormal cells, such as cancer cells.

The term "pharmacological composition" or "pharmaceutical formulation" refers to a composition or formulation in a form suitable for administration, for example, systemic administration, into a cell or patient, preferably a human. Suitable forms depend, in part, upon the use or the route of entry, for example oral, transdermal, or by injection. Such forms should not prevent the composition or formulation to reach a target cell (i.e., a cell to which the negatively charged polymer is targeted).

Other features and advantages of the invention will be apparent from the following description of the preferred embodiments and from the claims.

Administration

The mAb, mAb conjugates, mAb compounds and compositions of the instant invention can be used to administer pharmaceutical agents. Pharmaceutical agents prevent, inhibit the occurrence of, and/or treat (alleviate) one or more symptoms, preferably all of the symptoms, of a disease state in a patient or subject. The administration of pharmaceutical agents can be therapeutic and/or prophylactic.

Generally, the mAb compounds of the present invention are introduced by any standard means, with or without stabilizers, buffers, and the like, to form a pharmaceutical composition. For a liposome delivery mechanism, standard protocols for formation of liposomes can be followed. The compositions of the present invention can also be formulated and used as tablets; capsules; elixirs for oral administration; suppositories for rectal administration; sterile solutions; suspensions for injectable administration; and the like.

The present invention also includes pharmaceutically acceptable formulations of the compounds described above, preferably in combination with the molecule(s) to be delivered. These formulations include salts of the above compounds, e.g., acid addition salts, for example, salts of hydrochloric, hydrobromic, acetic acid, benzene sulfonic acid, and the like.

In one embodiment, the invention features the use of the mAb compounds of the invention in a composition comprising surface-modified liposomes containing polyol (ethylene glycol) lipids (PEG-modified, or long-circulating liposomes or stealth liposomes). In another embodiment, the invention features the use of mAb compounds of the invention covalently attached to polyethylene glycol. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (see for example Lasic et al. Chem. Rev. 1995, 95, 2601–2627; Ishiwata et al., Chem. Pharm. Bull. 1995, 43, 1005–1011). Such compositions have been shown to accumulate selectively in tumors, presumably by extravasation and capture in the neovascularized target tissues (see for example Lasic et al., Science 1995, 267, 1275–1276; Oku et al.,1995, Biochim. Biophys. Acta, 1238, 86–90). The long-circulating compositions enhance the pharmacokinetics and pharmacodynamics of therapeutic compounds, such as DNA and RNA, particularly compared to conventional cationic liposomes which are known to accumulate in tissues of the MPS (see for example Liu et al., J. Biol. Chem. 1995, 42, 24864–24870; Choi et al., International PCT Publication No. WO 96/10391; Ansell et al., International PCT Publication No. WO 96/10390; Holland et al., International PCT Publication No. WO 96/10392). Long-circulating compositions are also likely to protect drugs from nuclease degradation to a greater extent compared to cationic liposomes, based on their ability to avoid accumulation in metabolically aggressive MPS tissues such as the liver and spleen.

The present invention also includes one or more compositions prepared for storage or administration that include a pharmaceutically effective amount of the desired compound(s) in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro, Ed., 1985) hereby incorporated by reference herein. For example, preservatives, stabilizers, dyes and flavoring agents can be included in the composition. Examples of such agents include, but are not limited to, sodium benzoate, sorbic acid and esters of p-hydroxybenzoic acid. In addition, antioxidants and suspending agents can be included in the composition.

A pharmaceutically effective dose is that dose required to prevent, inhibit the occurrence of, and/or treat (alleviate) one or more symptoms, preferably all of the symptoms, of a disease state in a patient or subject. The dose can be therapeutic and/or prophylactic. The pharmaceutically effective dose depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 100 mg/kg body weight/day of active ingredients is administered dependent upon potency of the negatively charged polymer. Furthermore, the compounds of the invention and formulations thereof can be administered to a fetus via administration to the mother of a fetus.

The mAb compounds of the invention and formulations thereof can be administered orally, topically, parenterally, by inhalation or spray or rectally in dosage unit formulations containing conventional non-toxic pharmaceutically acceptable carriers, adjuvants, vehicles, and the like. The term parenteral as used herein includes percutaneous, subcutaneous, intravascular (e.g., intravenous), intramuscular, or intrathecal injection or infusion techniques and the like. In addition, there is provided a pharmaceutical formulation comprising a mAb, mAb conjugate or mAb compound of the invention and a pharmaceutically acceptable carrier. One or more mAbs, mAb conjugates, or mAb compounds of the invention can be present in association with one or more non-toxic pharmaceutically acceptable carriers and/or diluents and/or adjuvants, and if desired other active ingredients. The pharmaceutical compositions containing nucleic acid molecules of the invention can be in a form suitable for oral use, for example, as tablets, troches, lozenges, aqueous or oily suspensions, dispersible powders or granules, emulsion, hard or soft capsules, syrups, elixirs and the like.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or coated by known techniques. Such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients can be suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also comprise one or more preservatives, for example ethyl, or n-propyl p-hydroxybenzoate, one or more coloring agents, one or more flavoring agents, and/or one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring, coloring agents, and the like can also be present.

Pharmaceutical compositions of the invention can also be in the form of oil-in-water emulsions. The oil phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example, sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example, as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono-or diglycerides. In addition, fatty acids such as oleic acid find use in the preparation of injectables.

The compounds of the invention can also be administered in the form of suppositories, e.g., for rectal administration of the drug. These compositions can be prepared by mixing the drug with a suitable non-irritating excipient that is solid at ordinary temperatures, but liquid at the rectal temperature and will therefore melt in the rectum to release the drug. Such materials include, for example, cocoa butter and polyethylene glycols.

Compounds of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that can be combined with the carrier materials to produce a single dosage form will vary depending upon the patient or subject treated and the particular mode of administration. Dosage unit forms will generally contain from about 1 mg to about 500 mg of active ingredient.

It will be understood, however, that the specific dose level for any particular patient or subject will depend upon a variety of factors, including, but not limited to, the activity of the specific compound employed, the age, body weight, general health, sex, diet, time of administration, route of administration, and rate of excretion, drug combination, the severity of the particular disease undergoing therapy, and the like.

For administration to non-human animals, the composition can also be added to the animal feed or drinking water. For example, animal feed and drinking water compositions can be formulated so that the animal takes in a therapeutically appropriate quantity of the composition along with its diet. The composition can also be formulated as a premix for addition to the feed or drinking water.

The compounds of the present invention can also be administered to a patient or subject in combination with other therapeutic compounds to increase the overall therapeutic effect. The use of multiple compounds to treat an indication can increase the beneficial effects while reducing the presence of side effects.

Synthesis of Nucleic Acid Molecules

Synthesis of nucleic acids greater than 100 nucleotides in length is difficult using automated methods, and the cost of such molecules is prohibitive. In this invention, small nucleic acid motifs ("small" refers to nucleic acid motifs less than about 100 nucleotides in length, preferably less than about 80 nucleotides in length, and more preferably less than about 50 nucleotides in length; e.g., antisense oligonucleotides, hammerhead or NCH ribozymes) are preferably used for exogenous delivery. The simple structure of these molecules increases the ability of the nucleic acid to invade targeted regions of RNA structure. Exemplary molecules of the instant invention are chemically synthesized, and others can similarly be synthesized.

Oligonucleotides (for example DNA) are synthesized using protocols known in the art as described in Caruthers et al., 1992, *Methods in Enzymology* 211, 3–19, Thompson et al., International PCT Publication No. WO 99/54459, Wincott et al., 1995, *Nucleic Acids Res.* 23, 2677–2684, Wincott et al., 1997, *Methods Mol. Bio.,* 74, 59, Brennan et al., 1998, *Biotechnol Bioeng.,* 61, 33–45, and Brennan, U.S. Pat. No. 6,001,311. All of these references are incorporated herein by reference. The synthesis of oligonucleotides makes use of common nucleic acid protecting and coupling groups, such as dimethoxytrityl at the 5'-end, and phosphoramidites at the 3'-end. In a non-limiting example, small scale syntheses are conducted on standard equipment (e.g., a 394 Applied Biosystems, Inc. synthesizer) using a 0.2 μmol scale protocol with a 2.5 min coupling step for 2'-O-methylated nucleotides and a 45 sec coupling step for 2'-deoxy nucleotides. Table 1 outlines the amounts and the contact times of the reagents used in the synthesis cycle.

TABLE 1

A. 2.5 μmol Synthesis Cycle ABI 394 Instrument

| Reagent | Equivalents | Amount | Wait Time* DNA | Wait Time* 2'-O-methyl | Wait Time* RNA |
|---|---|---|---|---|---|
| Phosphoramidites | 6.5 | 163 μL | 45 sec | 2.5 min | 7.5 min |
| S-Ethyl Tetrazole | 23.8 | 238 μL | 45 sec | 2.5 min | 7.5 min |
| Acetic Anhydride | 100 | 233 μL | 5 sec | 5 sec | 5 sec |
| N-Methyl Imidazole | 186 | 233 μL | 5 sec | 5 sec | 5 sec |
| TCA | 176 | 2.3 mL | 21 sec | 21 sec | 21 sec |
| Iodine | 11.2 | 1.7 mL | 45 sec | 45 sec | 45 sec |
| Beaucage | 12.9 | 645 μL | 100 sec | 300 sec | 300 sec |
| Acetonitrile | NA | 6.67 mL | NA | NA | NA |

TABLE 1-continued

| B. 0.2 μmol Synthesis Cycle ABI 394 Instrument | | | | | |
|---|---|---|---|---|---|
| Reagent | Equivalents | Amount | Wait Time* DNA | Wait Time 2'-O-methyl | Wait Time* RNA |
| Phosphoramidites | 15 | 31 μL | 45 sec | 233 sec | 465 sec |
| S-Ethyl Tetrazole | 38.7 | 31 μL | 45 sec | 233 min | 465 sec |
| Acetic Anhydride | 655 | 124 μL | 5 sec | 5 sec | 5 sec |
| N-Methyl Imidazole | 1245 | 124 μL | 5 sec | 5 sec | 5 sec |
| TCA | 700 | 732 μL | 10 sec | 10 sec | 10 sec |
| Iodine | 20.6 | 244 μL | 15 sec | 15 sec | 15 sec |
| Beaucage | 7.7 | 232 μL | 100 sec | 300 sec | 300 sec |
| Acetonitrile | NA | 2.64 mL | NA | NA | NA |

| C. 0.2 μmol Synthesis Cycle 96 well Instrument | | | | | |
|---|---|---|---|---|---|
| Reagent | Equivalents: DNA/ 2'-O-methyl/Ribo | Amount: DNA/2'-O-methyl/Ribo | Wait Time* DNA | Wait Time* 2'-O-methyl | Wait Time* Ribo |
| Phosphoramidites | 22/33/66 | 40/60/120 μL | 60 sec | 180 sec | 360 sec |
| S-Ethyl Tetrazole | 70/105/210 | 40/60/120 μL | 60 sec | 180 min | 360 sec |
| Acetic Anhydride | 265/265/265 | 50/50/50 μL | 10 sec | 10 sec | 10 sec |
| N-Methyl Imidazole | 502/502/502 | 50/50/50 μL | 10 sec | 10 sec | 10 sec |
| TCA | 238/475/475 | 250/500/500 μL | 15 sec | 15 sec | 15 sec |
| Iodine | 6.8/6.8/6.8 | 80/80/80 μL | 30 sec | 30 sec | 30 sec |
| Beaucage | 34/51/51 | 80/120/120 | 100 sec | 200 sec | 200 sec |
| Acetonitrile | NA | 1150/1150/1150 μL | NA | NA | NA |

*Wait time does not include contact time during delivery.

Alternatively, syntheses at the 0.2 μmol scale can be performed on a 96-well plate synthesizer, such as the instrument produced by Protogene (Palo Alto, Calif.) with minimal modification to the cycle. In a non-limiting example, a 33-fold excess (60 μL of 0.11 M=6.6 μmol) of 2'-O-methyl phosphoramidite and a 105-fold excess of S-ethyl tetrazole (60 μL of 0.25 M=15 μmol) can be used in each coupling cycle of 2'-O-methyl residues relative to polymer-bound 5'-hydroxyl. In a non-limiting example, a 22-fold excess (40 μL of 0.11 M=4.4 μmol) of deoxy phosphoramidite and a 70-fold excess of S-ethyl tetrazole (40 μL of 0.25 M=10 μmol) can be used in each coupling cycle of deoxy residues relative to polymer-bound 5'-hydroxyl. Average coupling yields on a 394 Applied Biosystems, Inc. synthesizer, determined by colorimetric quantitation of the trityl fractions, are typically 97.5–99%. Other oligonucleotide synthesis reagents for a 394 Applied Biosystems, Inc. synthesizer include, but are not limited to: detritylation solution is 3% TCA in methylene chloride (ABI); capping is performed with 16% N-methyl imidazole in THF (ABI) and 10% acetic anhydride/10% 2,6-lutidine in THF (ABI); and oxidation solution is 16.9 mM $I_2$, 49 mM pyridine, 9% water in THF (PERSEPTIVE™). High quality acetonitrile (e.g., Burdick & Jackson Synthesis Grade) can be used directly from the reagent bottle. S-Ethyltetrazole solution (0.25 M in acetonitrile) can be made up from the solid obtained from standard suppliers (e.g., American International Chemical, Inc.). Alternately, for the introduction of phosphorothioate linkages, Beaucage reagent (3H-1,2-Benzodithiol-3-one 1,1-dioxide, 0.05 M in acetonitrile) is used.

Deprotection of the DNA oligonucleotides can be performed as follows: the polymer-bound trityl-on oligoribonucleotide is transferred to a 4 mL glass screw top vial and suspended in a solution of 40% aq. methylamine (1 mL) at 65° C. for 10 min. After cooling to −20° C., the supernatant is removed from the polymer support. The support is washed three times with 1.0 mL of EtOH:MeCN:H2O/3:1:1, vortexed and the supernatant is then added to the first supernatant. The combined supernatants, containing the oligoribonucleotide, are dried to a white powder. Standard drying or lyophilization methods known to those skilled in the art can be used.

The method of synthesis used for normal RNA including certain enzymatic nucleic acid molecules follows the procedure as described in Usman et al., 1987, *J Am. Chem. Soc.,* 109, 7845; Scaringe et al., 1990, *Nucleic Acids Res.,* 18, 5433; and Wincott et al., 1995, *Nucleic Acids Res.* 23, 2677–2684 Wincott et al., 1997, *Methods Mol. Bio.,* 74, 59, and makes use of common nucleic acid protecting and coupling groups, such as dimethoxytrityl at the 5'-end, and phosphoramidites at the 3'-end. In a non-limiting example, small scale syntheses are conducted on standard equipment (e.g., a 394 Applied Biosystems, Inc. synthesizer) using a 0.2 μmol scale protocol with a 7.5 min coupling step for alkylsilyl protected nucleotides and a 2.5 min coupling step for 2'-O-methylated nucleotides. Table 1 outlines the amounts and the contact times of the reagents used in the synthesis cycle. Alternatively, syntheses at the 0.2 μmol scale can be done on a 96-well plate synthesizer, such as the instrument produced by Protogene (Palo Alto, Calif.) with minimal modification to the cycle. A 33-fold excess (60 μL of 0.11 M=6.6 μmol) of 2'-O-methyl phosphoramidite and a 75-fold excess of S-ethyl tetrazole (60 μL of 0.25 M=15 μmol) can be used in each coupling cycle of 2'-O-methyl residues relative to polymer-bound 5'-hydroxyl. A 66-fold excess (120 μL of 0.11 M=13.2 μmol) of alkylsilyl (ribo) protected phosphoramidite and a 150-fold excess of S-ethyl tetrazole (120 μL of 0.25 M=30 μmol) can be used in each coupling cycle of ribo residues relative to polymer-bound 5'-hydroxyl. Average coupling yields on a 394 Applied Biosystems, Inc. synthesizer, determined by colorimetric quantitation of the trityl fractions, are typically 97.5–99%. Other oligonucleotide synthesis reagents for a 394 Applied Biosystems, Inc. synthesizer include: detritylation solution is 3% TCA in methylene chloride (ABI); capping is performed with 16% N-methyl imidazole in THF (ABI) and 10% acetic anhydride/10% 2,6-lutidine in THF (ABI); oxidation solution is 16.9 mM $I_2$, 49 mM pyridine, 9% water in THF (PERSEPTIVE™). High quality acetonitrile (e.g., Burdick & Jackson Synthesis Grade) can be used directly from the reagent bottle. S-Ethyltetrazole solution (0.25 M in acetonitrile) can be made up from the solid obtained from standard suppliers (e.g., American International Chemical, Inc.). Alternately, for the introduction of phosphorothioate linkages, Beaucage reagent (3H-1,2-Benzodithiol-3-one 1,1-dioxide0.05 M in acetonitrile) can be used.

Deprotection of the RNA can be performed using either a "two-pot" or "one-pot" protocol as follows. For the two-pot protocol, the polymer-bound trityl-on oligoribonucleotide is transferred to a 4 mL glass screw top vial and suspended in a solution of 40% aqueous (aq.) methylamine (1 mL) at 65° C. for 10 min. After cooling to −20° C., the supernatant is removed from the polymer support. The support is washed three times with 1.0 mL of EtOH:MeCN:H2O/3:1:1, vortexed and the supernatant is then added to the first supernatant. The combined supernatants, containing the oligoribonucleotide, are dried to a white powder. The base deprotected oligoribonucleotide is resuspended in anhydrous TEA/HF/NMP solution (300 μL of a solution of 1.5 mL N-methylpyrrolidinone, 750 μL TEA and 1 mL TEA•3HF to provide a 1.4 M HF concentration) and heated to 65° C. After 1.5 h, the oligomer is quenched with 1.5 M $NH_4HCO_3$.

Alternatively, for the one-pot protocol, the polymer-bound trityl-on oligoribonucleotide is transferred to a 4 mL glass screw top vial and suspended in a solution of 33% ethanolic methylamine/DMSO: 1/1 (0.8 mL) at 65° C. for 15 min. The vial is brought to r.t. TEA•3HF (0.1 mL) is added and the vial is heated at 65° C. for 15 min. The sample is cooled at −20° C. and then quenched with 1.5 M $NH_4HCO_3$.

For purification of the trityl-on oligomers, the quenched $NH_4HCO_3$ solution can be loaded onto a C-18 containing cartridge that had been prewashed with acetonitrile followed by 50 mM TEAA. After washing the loaded cartridge with water, the RNA can be detritylated with 0.5% TFA for 13 min. The cartridge can then be washed again with water, salt exchanged with 1 M NaCl and washed with water again. The oligonucleotide can then be eluted with 30% acetonitrile.

Inactive hammerhead ribozymes or binding attenuated control ((BAC) oligonucleotides) can be synthesized by substituting a U for $G_5$ and a U for $A_{14}$ (numbering from Hertel, K. J., et al., 1992, *Nucleic Acids Res.,* 20, 3252). Similarly, one or more nucleotide substitutions can be introduced in other enzymatic nucleic acid molecules to inactivate the molecule and such molecules can serve as a negative control.

The average stepwise coupling yields are typically >98% (Wincott et al., 1995 *Nucleic Acids Res.* 23, 2677–2684). Those of ordinary skill in the art will recognize that the scale of synthesis can be adapted to be larger or smaller than the example described above including, but not limited to, 96 well format, with the ratio of chemicals used in the reaction being adjusted accordingly.

Alternatively, the nucleic acid molecules of the present invention can be synthesized separately and joined together post-synthetically, for example by ligation (Moore et al., 1992, *Science* 256, 9923; Draper et al., International PCT publication No. WO 93/23569; Shabarova et al., 1991, *Nucleic Acids Research* 19, 4247; Bellon et al., 1997, *Nucleosides & Nucleotides,* 16, 951; Bellon et al., 1997, *Bioconjugate Chem.* 8, 204).

The nucleic acid molecules of the present invention can be modified extensively to enhance stability by modification with nuclease resistant groups, for example, 2'-amino, 2'-C-allyl, 2'-flouro, 2'-O-methyl, 2'-H (for a review see Usman and Cedergren, 1992, *TIBS* 17, 34; Usman et al., 1994, *Nucleic Acids Symp. Ser.* 31, 163). Ribozymes can be purified by gel electrophoresis using methods known in the art or purified by high pressure liquid chromatography (HPLC; See Wincott et al., Supra, the totality of which is hereby incorporated herein by reference) and can be re-suspended in water.

Indications

Particular disease states that can be treated using compounds and compositions of the invention include, but are not limited to, cancers and cancerous conditions such as breast, lung, prostate, colorectal, brain, esophageal, stomach, bladder, pancreatic, cervical, head and neck, and ovarian cancer, melanoma, lymphoma, glioma, multidrug resistant cancers, and/or viral infections including HIV, HBV, HCV, CMV, RSV, HSV, poliovirus, influenza, rhinovirus, west Nile virus, Ebola virus, foot and mouth virus, and papilloma virus infection.

The molecules of the invention can be used in conjunction with other known methods, therapies, or drugs. For example, the use of monoclonal antibodies (e.g.; mAb IMC C225, mAb ABX-EGF) treatment, tyrosine kinase inhibitors (TKIs), for example OSI-774 and ZD1839, chemotherapy, and/or radiation therapy, are all non-limiting examples of methods that can be combined with or used in conjunction with the compounds of the instant invention. Common chemotherapies that can be combined with nucleic acid molecules of the present invention include, but are not limited to, various combinations of cytotoxic drugs to kill cancer cells. These drugs include, but are not limited to, paclitaxel (Taxol), docetaxel, cisplatin, methotrexate, cyclophosphamide, doxorubin, fluorouracil carboplatin, edatrexate, gemcitabine, vinorelbine, and the like. Those skilled in the art will recognize that other drug compounds and therapies can be similarly and readily combined with the compounds of the instant invention and are hence within the scope of the instant invention.

Diagnostic Uses

The compounds of the present invention, for example, monoclonal antibodies and/or mAb nucleic acid conjugate molecules, can be used as diagnostic tools to detect the presence of a nucleic acid molecule in a biological system or sample. Specifically, compounds of the invention are used to detect nucleic acid molecules without the need for labeling the nucleic acid molecules of interest. This feature is especially important during clinical trials in which nucleic acid therapeutics need to be assayed to determine the pharmacokinetic and metabolic properties of these compounds. In preclinical development of nucleic acid therapeutics, tagged versions of the nucleic acid therapeutic are typically used to evaluate the in vivo characteristics of a particular compound. However, during clinical trials in humans, such tags cannot be used. Monoclonal antibodies of the invention are therefore useful in bioanalytical applications as diagnostic reagents. These antibodies are used to detect the presence of target nucleic acid molecules in samples derived from a variety of sources, including biological samples derived from a patient or subject in a clinical trial. As such, the antibodies of the invention can be used to quantitate the amount of nucleic acid therapeutic in a sample. Methods of quantitation using antibody systems are known in the art, see for example Johansen et al., U.S. Pat. No. 6,087,188;

Ramakrishnan, U.S. Pat. No. 5,395,938; and Fujisawa, et al., U.S. Pat. No. 5,028,524; all incorporated by reference herein.

EXAMPLE 1

Development of a CA1USR antibody specific for 2'-deoxy-2'-C-allyl Uridine Containing Nucleic Acid Molecules As the ANGIOZYME® ribozyme therapeutic has moved through preclinical studies and into clinical trials, the need has arisen for a reagent to detect this molecule in blood and tissue samples. For preclinical studies, addition of tags such as 2' bromo-deoxyuridine (BrdU) and fluorescein to the ribozyme during synthesis is useful for localization studies. In clinical trials, however, the ribozymes administered therapeutically do not carry such tags. For clinical localization studies, a monoclonal antibody (mAb) was developed to recognize the non-native 2'-deoxy-2'-C-allyl Uridine modification that is present at a single site in the ANGIOZYME® ribozyme therapeutic. The data presented herein show that the mAb CA1USR, has a high degree of affinity for the 2'-deoxy-2'-C-allyl Uridine modification. Nucleotides that do not contain the 2'-deoxy-2'-C-allyl Uridine modification were incapable of competing for the binding of the CA1USR mAb to 2'-deoxy-2'-C-allyl Uridine coupled to protein. Replacement of 2'-deoxy-2'-C-allyl Uridine with any of a series of commonly employed nucleotide modifications drastically reduced mAb binding, which implies that the epitope seen by CA1USR comprises both the C-allyl modification and uridine. Finally, the mAb was used to directly localize two structurally different ribozymes containing the 2'-deoxy-2'-C-allyl Uridine modification in the kidneys of mice treated with the ribozymes, and its utility demonstrated as an in vivo detection reagent.

Conjugation of 2'-deoxy-2'-C-allyl Uridine To Proteins.

2'-deoxy-2'-C-allyl Uridine 5'-phosphate was synthesized from 2'-deoxy-2'-C-allyl Uridine (Beigelman et al., 1995, *Nucleic Acids Research,* 23, 4434) by the method of Yoshikawa (Yoshikawa et al., 1969, *Bull. Chem. Japan,* 42, 3505) with subsequent purification on DEAE Sephadex using a gradient of TEAB (0–0.4 M). The resulting yield was 80% (31P NMR δ=29.3 ppm). 2'-deoxy-2'-C-allyl Uridine 5'-phosphate was covalently coupled to either bovine serum albumin (BSA) or keyhole lympet hemocyanin (KLH) through the phosphate group of the nucleotide to primary amines of the protein by carbodiimide chemistry with 1-ethyl-3-diisopropylaminocarbodiimide-HCl (EDC) The method used here was modified from the method published by Halloran and Parker (Halloran and Parker, 1966, *J. Immunol.,* 6, 373) as follows: BSA was dissolved in 10 mM Tris-HCl, pH 7.5, to a concentration of 125 mg/ml; 2'-C-allyl-Uridine 5'-phosphate at a concentration of 216.67 mg/ml in water was adjusted to pH 7.5 with 5N NaOH. A 300 μl volume of 2'-deoxy-2'-C-allyl Uridine was mixed with 200 μl of the BSA solution; 65 μl of EDC at 1 g/ml was added (=65 mg) and the reaction was incubated for 24 h at room temperature in the dark. The solution was dialyzed at room temperature against multiple changes of 10 mM Tris, pH 7.5, until the spectrophotometric profile of a separate "mock" reaction (nucleotide and protein without EDC) was the same as that of the protein alone. For coupling of 2'-deoxy-2'-C-allyl Uridine 5'-phosphate to KLH, the concentrations of nucleotide and protein were reduced to 10 mg and 3.85 mg, respectively; 100 mg of EDC was added; the total volume of the reaction was adjusted to 500 ul with 10 mM Tris, pH 7.5. The remainder of the procedure was identical to that for the BSA coupling.

Monoclonal Antibody Production.

Twelve week-old female SJL/Jax mice were immunized in the left hind footpad with 100 μg 2'-deoxy-2'-C-allyl Uridine-conjugated BSA (based on concentration of BSA) emulsified in Complete Freund's Adjuvant (total volume of 25 μl). Subsequent immunizations were administered at the same site with a minimum interval of two weeks. The second immunization was of 100 μg of conjugate in Incomplete Freund's Adjuvant (IFA); the third immunization consisted of 200 μg of unconjugated 2'-deoxy-2'-C-allyl Uridine in IFA. Three days after a fourth immunization with 100 μg 2'-C-allyl U-conjugated BSA in IFA, the popliteal lymph node was removed and fused with the 653 myeloma. Fusion products were plated in 96 well plates, and supernatants were screened for specific anti-2'-deoxy-2'-C-allyl Uridine activity, as described below. Positive hybrids were cloned in soft agar.

Fusion Screening Assay.

N-oxy-succinimide ester derivatized 96 well plates (DNA-Bind; Costar/Corning, Corning, N.Y.) were coated overnight at room temperature with 50 ng/well of 2'-deoxy-2'-C-allyl Uridine-KLH. After two washes with phosphate buffered saline, 0.1% Tween (PBS-T), plates were blocked for 1 h with PBS plus 1% casein (Pierce, Rockford, Ill.). Hybridoma supernatant was incubated on the plates for 1 h, after which wells were washed 4 times with PBS-T. Positive wells were detected with peroxidase-conjugated F(ab)'2 Goat anti-mouse IgG (Pel-Freez, Rogers, Ark.), and developed with TMB substrate (Kirkegaard and Perry, 2 component; Gaithersburg, Md.). Plates were read on a Molecular Dynamics plate reader (Molecular Dynamics, Sunnyvale, Calif.) at 450 nm with 595 nm correction.

Competition Enzyme Immunoassay (EIA)

DNA-Bind plates were coated overnight with 50 ng/well of 2'-deoxy-2'-C-allyl Uridine-conjugated KLH. 60 μl volumes of the purified CA1USR mAb, at a concentration of 500 ng/ml, were incubated at 37° C. for 30 min with 60 μl volumes of a series of concentrations of competitor nucleotides, from a concentration of 500 to 7.8 μg/ml. The antibody-competitor mixtures were then plated on the 2'-C-allyl-KLH coated DNA-Bind plates, and the EIA proceeded as described for the fusion screening assay.

EIA on Biotinylated C-allyl Oligonucleotides and Ribozymes.

Oligonucleotides and ribozymes were synthesized with biotin at one end, then bound to streptavidin plates (Hi-Bind Streptavidin plates; Roche Molecular Systems, Indianapolis, Ind.) for 1 h at room temperature. CA1USR MAb was added at 1 μg/ml, and incubated for 1 h. The remainder of the EIA proceeded as described in the fusion screening assay.

Immunohistochemistry.

Tissues were harvested from mice injected subcutaneously with either saline or a ribozyme from 60 to 120 min after injection. Animals were perfused with normal saline, then with a solution of 3% paraformaldehyde, 0.5% gluteraldehyde prior to tissue harvest. The tissue was placed in a 30% sucrose solution at 4° C. overnight, then removed, and frozen in a Gentle Jane (Instrumedics; Hackensack, N.J.) Snap-Freezing System with Cryo-Gel Embedding Medium (Instrumedics). Five micron (μm) sections were cut and placed on slides; the slides were allowed to air dry. Prior to staining, slides were quenched in 3% hydrogen peroxide and 0.5% horse serum in PBS, then blocked with M.O.M. Mouse Ig Blocking Reagent (Vector Labs, Burlingame, Calif.) for 1 h, washed with PBS, and stained with the CA1USR MAb at 5 μg/ml in M.O.M. diluent for 30 min. After washing, slides were incubated with M.O.M. Biotinylated Anti-Mouse IgG Reagent for 10 min, washed, and incubated with Vectastain Elite ABC Reagent for 5 min, then developed in DAB chromogen (Vector Labs). Slides were rinsed, counter-stained with hematoxylin (Richard-Allan Scientific, Kalamazoo, Mich.), dehydrated, and cover-slipped. Slides were viewed on a Nikon Microphot FXA microscope.

Results

FIG. 1 depicts the chemical structure of the 5' phosphate of 2'-deoxy-2'-C-allyl Uridine. The molecule was conjugated to either BSA or KLH by EDC. Removal of free from protein-bound 2'-deoxy-2'-C-allyl Uridine phosphate was accomplished by extensive dialysis. Dialysis was considered complete when the OD260/280 was the same for protein alone as that of mock 2'-deoxy-2'-C-allyl Uridine 5'-phosphate-conjugated protein (2'-deoxy-2'-C-allyl Uridine 5'-phosphate and protein without EDC). The degree of substitution on the individual proteins was estimated by the molar concentration of the protein and nucleotide based on the OD280 and extinction coefficient for the protein and OD260 and extinction coefficient for 2'-deoxy-2'-C-allyl Uridine. The degree of substitution for the 2'-deoxy-2'-C-allyl Uridine-BSA conjugate used for immunization is estimated to be 5 molecules of 2'-deoxy-2'-C-allyl Uridine per molecule of BSA. For KLH, which displays molecular weight heterogeneity, the degree of substitution was estimated to be from 70 to 200 molecules of 2'-deoxy-2'-C-allyl Uridine per molecule of KLH. A hybrid binding to 2'-deoxy-2'-C-allyl Uridine-KLH was identified and cloned. The clone, termed CA1USR, is a murine IgGlk.

For determination of fine specificity of CA1USR, a series of nucleotides of structure similar to 2'-deoxy-2'-C-allyl Uridine were used to inhibit the binding of the CA1USR mAb to 2'-deoxy-2'-C-allyl Uridine-coupled KLH captured on DNA-Bind plates. Results are presented in FIG. 2. Of six different uridine nucleotides, only 2'-deoxy-2'-C-allyl Uridine was able to inhibit the binding of CA1USR mAb to 2'-deoxy-2'-C-allyl Uridine-KLH. Other nucleotides containing adenine, cytosine, or guanine had absolutely no ability to inhibit 2'-deoxy-2'-C-allyl Uridine mAb binding.

Figure 3:
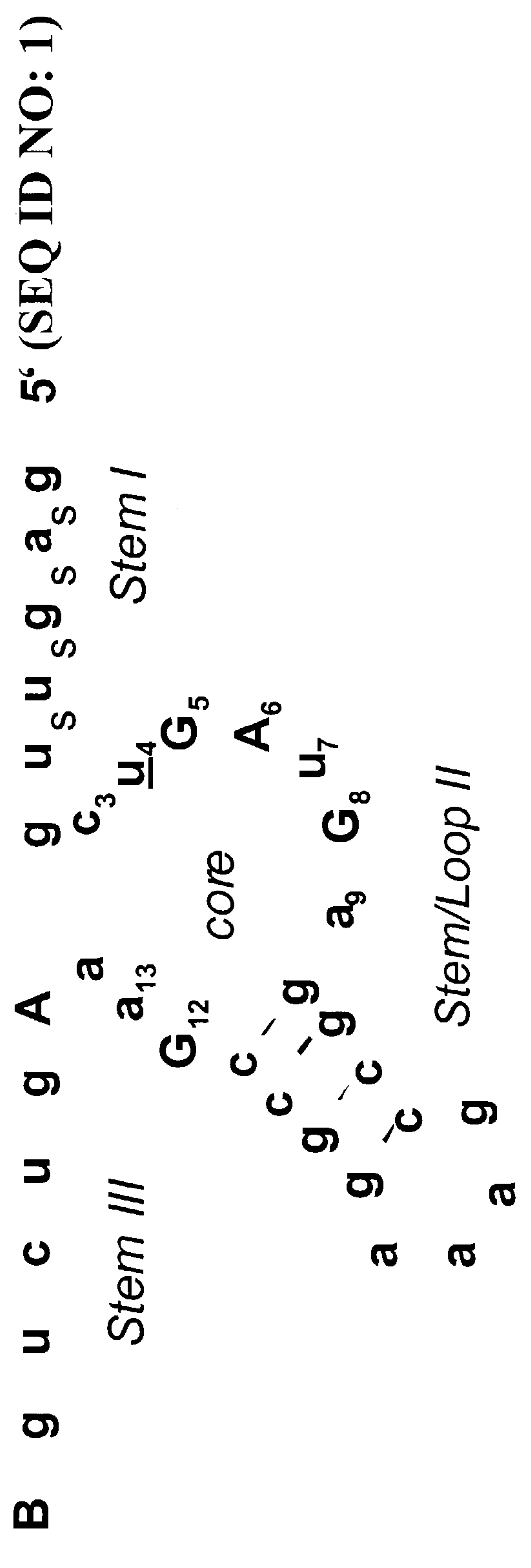
FIG. 3 shows the chemical structure of an ANGIOZYME® enzymatic nucleic acid (SEQ ID NO: 1).
Figure 4:
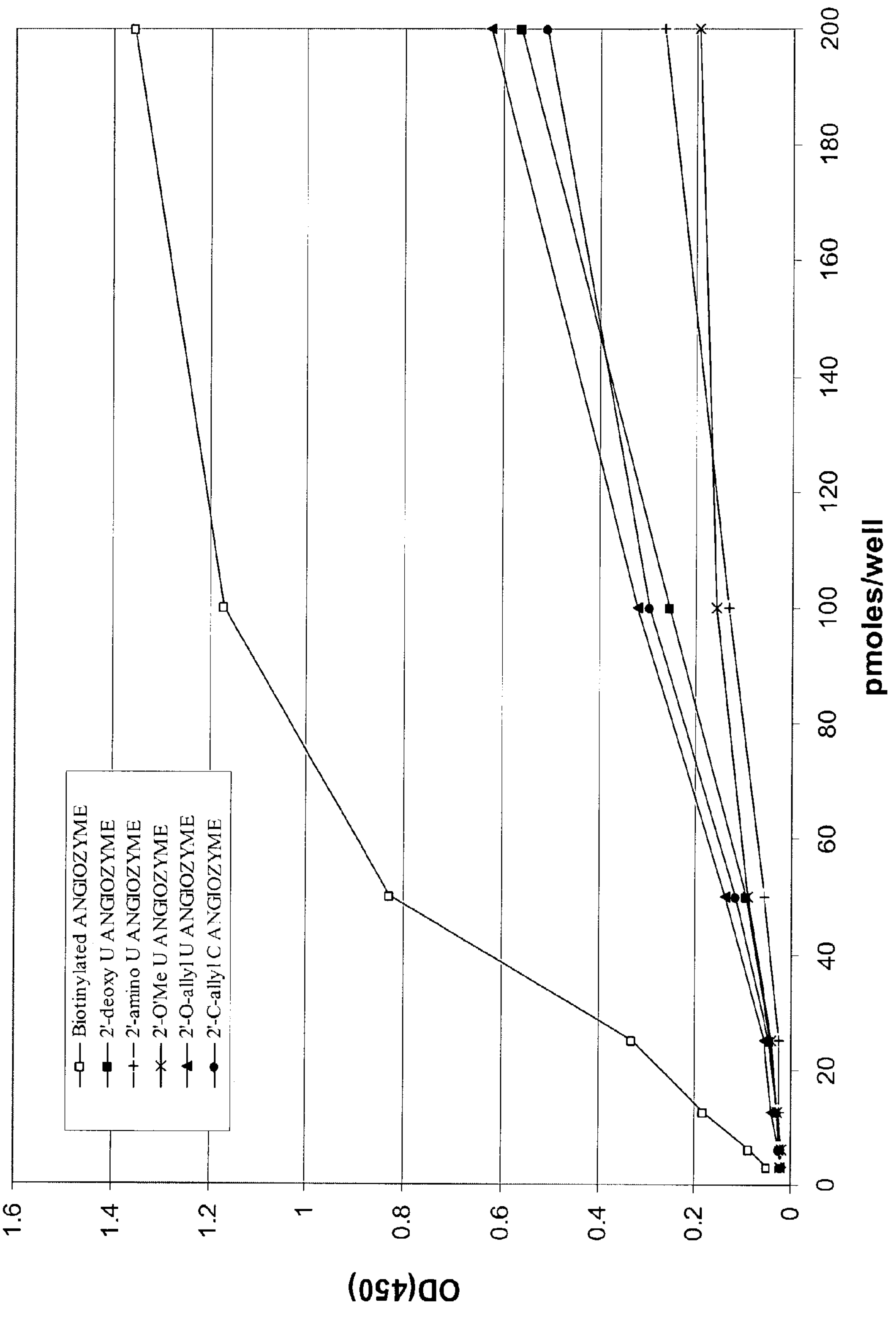
FIG. 4 shows binding of CA1USR to different modified enzymatic nucleic acid molecules. Biotinylated versions of a series of modified enzymatic nucleic acids were bound in equimolar concentrations to streptavidin wells, and binding of 1 μg/ml of purified CA1USR was determined. (□) indicates binding of biotinylated enzymatic nucleic acid molecule; (■) 2'-deoxy U enzymatic nucleic acid molecule; (+): 2'-amino U enzymatic nucleic acid molecule; (×): 2'-O Me U enzymatic nucleic acid molecule; (▲): 2'-O allyl U enzymatic nucleic acid molecule; (●): 2'-C-allyl C enzymatic nucleic acid molecule.

A synthetic ribozyme containing the 2'-deoxy-2'-C-allyl Uridine modification was utilized to determine whether the mAb binds this modification in the context of an oligonucleotide. The structure of the ANGIOZYME® ribozyme directed against VEGFR-1 mRNA is shown in FIG. 3. The ANGIOZYME® ribozyme is a synthetic 35-mer hammerhead ribozyme consisting of VEGFR-1 sequence-specific complementary binding arms, a catalytic core, and a stem-loop that confers the required structure for catalytic activity of the molecule. The 2'-deoxy-2'-C-allyl Uridine modification is shown in the molecule as U4, eight nucleotides from the 5' end. To further examine which components of 2'-deoxy-2'-C-allyl Uridine are essential for antibody binding, six different U4 2'-ribose modified ribozymes otherwise equivalent in sequence to the ANGIOZYME® ribozyme with biotin at the 5' end were synthesized: 2'-amino U, 2'-O-methyl Uridine, 2'-deoxy Uridine, 2'-O-allyl Uridine, and 2'-propyl Uridine (FIG. 1). In addition, a ribozyme having the same sequence as the ANGIOZYME® ribozyme but containing 2'-deoxy-2'-C-allyl Cytidine (FIG. 1) instead of 2'-deoxy-2'-C-allyl Uridine was synthesized. The biotinylated, modified ribozymes were added to streptavidin plates at equimolar concentrations to determine the ability of saturating concentrations of the CA1USR mAb to bind each ribozyme. Results are shown in FIG. 4.

The mAb binds the biotinylated ANGIOZYME® ribozyme well, in a concentration-dependent fashion. mAb binding is drastically reduced on an ANGIOZYME® ribozyme with modified uridines other than 2'-deoxy-2'-C-allyl at the U4 position. Of importance is the lack of binding by the mAb to an ANGIOZYME® ribozyme when 2'-C-allyl uridine is replaced by 2'C-allyl cytidine. The binding and competition experiments suggest that both the 2'-C-allyl modification and the Uracil nucleobase form the epitope that is recognized by the CA1USR mAb.

The CA1USR mAb was utilized to localize the ANGIOZYME® ribozyme in vivo, by immunohistochemistry on tissues from mice treated subcutaneously with either saline or the ANGIOZYME® ribozyme. In kidneys from animals administered 3 subcutaneous 100 mg/kg injections of the ANGIOZYME® ribozyme, intense 2'-deoxy-2'-C-allyl Uridine mAb immunoreactivity is evident in granular structures within the cytoplasm of cortical tubular epithelial cells. Hematoxylin and eosin microscopy of the ANGIOZYME® ribozyme-treated kidneys showed these granular structures to be basophilic in character. In contrast to the kidneys from the ANGIOZYME® ribozyme treated mice, those from saline treated mice demonstrated absolutely no staining with the CA1USR mAb.

Figure 5:
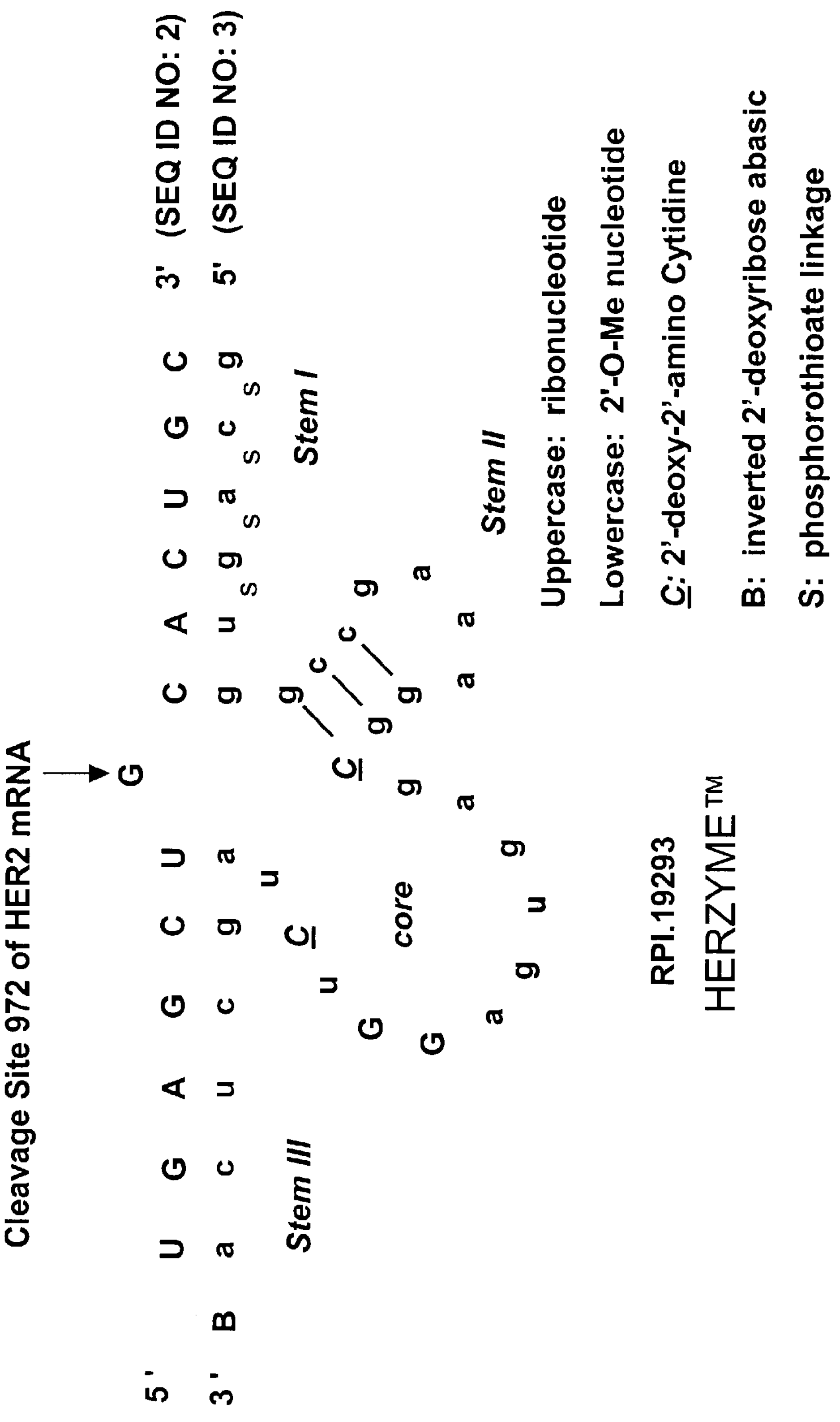
FIG. 5 shows the chemical structure of a HERZYME™ enzymatic nucleic acid (SEQ ID NO: 3).

The CA1USR mAb was further examined for its in vivo specificity. A ribozyme targeted to Her2 mRNA with a proposed two-dimensional structure different from the hammerhead motif of the ANGIOZYME® ribozyme was synthesized with the 2'-deoxy-2'-C-allyl modification at the U14 position. The structure of this ribozyme, which is designated by the trademark HERZYME™, is depicted in FIG. 5. Mice were injected subcutaneously three times with a concentration of 100 mg/kg of either the HERZYME™ ribozyme or the 2'-deoxy-2'-C-allyl U14 modified version of the HERZYME™ ribozyme to determine whether the CA1USR mAb could detect the modified ribozyme in vivo. CA1USR mAb stains granules in kidney cells from the 2'-C-allyl U14 modified version of the HERZYME™ ribozyme treated mice intensely, with no staining of the unmodified HERZYME™ ribozyme treated murine kidney cells.

As novel therapeutics based on nucleic acid chemistries move into preclinical and clinical studies, the need for reagents and methods of detection both in vitro and in vivo has become paramount to understanding their modes of action, localization, and other important parameters. Monoclonal antibodies provide useful tools for assay development. However, the generation of high affinity mAbs directed against nucleic acid structures has required overcoming immunological barriers. As a general rule, nucleic acids are non-immunogenic; this is probably due to mechanisms of immune tolerance that protect an organism from the pathologic consequences of autoimmune responses. Generation of high affinity mAb's to these structures requires overcoming an animal's natural mechanisms of tolerance. For this reason, applicant utilized the SJL strain of inbred mice, because they have been reported to generate autoantibodies to denatured DNA complexed with methylated BSA better than five other strains of mice, including the most common strain used for monoclonal antibody production, BALB/c (Kearney et al., 1979, *J. Immunol.,* 123, 1548). In fact, during the experiments to generate the 2'-deoxy-2'-C-allyl Uridine MAb described here, applicant immunized three different strains of mice: BALB/c, C57×BALB F1, and SJL; only SJL mice generated anti-2'-deoxy-2'-C-allyl Uridine mAbs. A second fusion with SJL mice also resulted in generation of a 2'-deoxy-2'-C-allyl Uridine mAb, but of apparent lower affinity than that described here.

Nucleic acids immunized into mice, even with Freund's Complete Adjuvant, behave as haptens, and, even in the SJL mice, resulted in mAb's of the IgM class, which can be less desirable than IgG's. Such small molecules generally require covalent coupling to a carrier protein, such as bovine serum albumin, keyhole limpet hemocyanin, or other carrier protein known in the art, for development of a mature, high affinity immune response. Several methods, including periodate oxidation of the nucleotide for activation and coupling, were used for generating mAbs to other modified nucleosides and nucleotides. mAbs generated by this coupling method include an antibody directed against bromodeoxyuridine and mAbs to methyl methyladenosine and deoxycytodine. Applicant favored the coupling of the phosphate group to primary amines of the carrier proteins through conjugation with EDC, since this conjugation does not affect the structure of either the ribose or base of the coupled nucleotide. This allows the animal to recognize the 2'-deoxy-2'-C-allyl Uridine in a structure more similar to its form in a ribozyme or other nucleic acid molecule.

Based on EIA results, the inferred specificity of the mAb appears to involve both the 2'-deoxy-2'-C-allyl modification and the uracil nucleobase. The inability of any other ribonucleotide to inhibit the binding of the mAb to 2'-deoxy-2'-C-allyl Uridine-coupled to KLH and the fact that the mAb binds very poorly to a ribozyme substituted with 2'-deoxy-2'-C-allyl Cytidine instead of 2'-deoxy-2'-C-allyl Uridine, suggest that both the 2'-deoxy-2'-C-allyl modification and uracil nucleobase are necessary for antibody binding.

Other mAbs have been generated to modified nucleotides, but few appear to have the exquisite specificity of the CA1USR mAb. A series of mAbs to either bromo-deoxy uridine or iodo-deoxy uridine have been generated, among them three mAbs termed IU-1, IU-4, and B-44, respectively. In contrast to the CA1USR mAb, whose epitope does not permit substitution of the 2'-C allyl-U modification, all of these antibodies recognize more than one halogen modification of deoxyuridine. The success of the CA1USR MAb in localizing two structurally different ribozymes containing the 2'-deoxy-2'-C-allyl Uridine modification in mouse kidney proximal tubules confirms its utility for in vivo localization. The results of the ANGIOZYME® ribozyme localization are consistent with those observed in immunohistochemical evaluation of a tetramethylrhodamine labeled form of the ANGIOZYME® ribozyme in murine kidneys. Such findings obviate the necessity for synthesizing different kinds of tagged ribozymes for localization studies in preclinical animal models of disease. Additionally, this mAb enables the localization of 2'-deoxy-2'-C-allyl Uridine-containing ribozymes in biopsies of patients treated with these ribozymes during clinical trials.

Similarly, the development of other monoclonal antibodies to recognize other unique nucleic acid molecules, based on recognition of particular nucleotides or recognition of the particular three dimensional structure of the entire nucleic acid molecule, can be developed using the methods of the instant invention. For example, the use of 2'-deoxy-2'-C-allyl Uridine in place of Uridine in a given nucleic acid molecule of interest can allow for detection of that nucleic acid molecule by CA1USR. Alternately, other monoclonal antibodies can be developed to recognize the unique structure of different nucleic acid molecules, such as enzymatic nucleic acid molecules having SEQ ID NOS: 1, 3, 16, or 17.

One skilled in the art would readily appreciate that the present invention is well adapted to carry out the objects and obtain the ends and advantages mentioned, as well as those inherent therein. The methods and compositions described herein are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that various substitutions and modifications can be made to the invention disclosed herein without departing from the scope and spirit of the invention. Thus, such additional embodiments are within the scope of the present invention and the following claims.

The invention illustratively described herein suitably can be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by various embodiments, optional features, modification and variation of the concepts herein disclosed can be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

We claim:

1. An isolated monoclonal antibody having binding affinity for a 2'-deoxy-2'-C-allyl Uridine nucleoside or 2'-deoxy-2'-C-allyl Uridine nucleotide of a nucleic acid molecule.

2. An isolated monoclonal antibody having binding affinity for a 2'-deoxy-2'-C-allyl Uridine nucleoside or 2'-deoxy-2'-C-allyl Uridine nucleotide of a nucleic acid molecule comprising SEQ ID NO: 1.

3. An isolated monoclonal antibody having binding affinity for a 2'-deoxy-2'-C-allyl Uridine nucleoside or 2'-deoxy-2'-C-allyl Uridine nucleotide of a nucleic acid molecule comprising SEQ ID NO: 3.

4. An isolated monoclonal antibody having binding affinity for a 2'-deoxy-2'-C-allyl Uridine nucleoside or 2'-deoxy-2'-C-allyl Uridine nucleotide of a nucleic acid molecule comprising SEQ ID NO: 16.

5. An isolated monoclonal antibody having binding affinity for a 2'-deoxy-2'-C-allyl Uridine nucleoside or 2'-deoxy-2'-C-allyl Uridine nucleotide of a nucleic acid molecule comprising SEQ ID NO: 17.

6. The isolated monoclonal antibody of any of claims 1–5, wherein said isolated monoclonal antibody is a murine IgG1k antibody.

7. A method for generating a monoclonal antibody (mAb) having the binding affinity of claim 1, the method comprising:
- (a) Conjugating a 2'-deoxy-2'-C-allyl Uridine nucleotide to a carrier protein, to form a nucleotide-protein conjugate;
- (b) Immunizing a SJL mouse the conjugate from (a);
- (c) Obtaining antibody producing cells from the immunized SJL mouse (b);
- (d) Fusing cells obtained from the SJL mouse of (b) with a myeloma cell under conditions suitable for generating a hybridoma; and
- (e) Using supernatant from the hybridoma of (d) in a fusion screen under conditions suitable for isolating the monoclonal antibody.

8. The method of claim 7, wherein the 2'-deoxy-2'-C-ally Uridine nucleotide of (a) is a 2'-deoxy-2'-C-allyl Uridine 5'-phosphate.

9. A method for generating a monoclonal antibody (mAb) having the binding affinity of claim 2, the method comprising:
- (a) Conjugating a nucleic acid molecule having SEQ ID NO: 1 to a carrier protein, to form a nucleic acid-protein conjugate;
- (b) Immunizing a SJL mouse with the conjugate from (a);
- (c) Obtaining antibody producing cells from the immunized SJL mouse of (b);
- (d) Fusing cells obtained from the SJL mouse of (b) with a myeloma under conditions suitable for generating a hybridoma; and
- (e) Using supernatant from the hybridoma of (d) in a fusion screen under conditions suitable for isolating the monoclonal antibody.

10. A method for generating a monoclonal antibody (mAb) having the binding affinity of claim 3, the method comprising:
- (a) Conjugating a nucleic acid molecule having SEQ ID NO: 3 to a protein, such as bovine serum albumin (BSA) or keyhole limpet hemocyanin (KLH), to form a nucleic acid-protein conjugate;
- (b) Immunizing a SJL mouse the conjugate from (a);
- (c) Obtaining antibody producing cells from the immunized SJL mouse of (b);
- (d) Fusing cells obtained from the SJL mouse (b) with a myeloma under conditions suitable for generating a hybridoma; and
- (e) Using supernatant from the hybridoma of (d) in a fusion screen under conditions suitable for isolating the monoclonal antibody.

11. A method for generating a monoclonal antibody (mAb) having the binding affinity of claim 4, the method comprising:
- (a) Conjugating a nucleic acid molecule having SEQ ID NO: 16 to a protein, such as bovine serum albumin (BSA) or keyhole limpet hemocyanin (KLH), to form a nucleic acid-protein conjugate;
- (b) Immunizing a SJL mouse with the conjugate from (a);
- (c) Obtaining antibody producing cells from the SJL mouse of (b);
- (d) Fusing cells obtained from the SJL mouse of (b) with a myeloma under conditions suitable for generating a hybridoma; and
- (e) Using supernatant from the hybridoma of (d) in a fusion screen under conditions suitable for isolating the monoclonal antibody.

12. A method for generating a monoclonal antibody (mAb) having the binding affinity of claim 5, the method comprising:
- (a) Conjugating a nucleic acid molecule having SEQ ID NO: 17 to a protein, such as bovine serum albumin (BSA) or keyhole limpet hemocyanin (KLH), to form a nucleic acid-protein conjugate;
- (b) Immunizing a SJL mouse with the conjugate from (a);
- (c) Obtaining antibody producing cells from the SJL mouse of (b);
- (d) Fusing a cells obtained from the SJL mouse (b) with a myeloma under conditions suitable for generating a hybridoma; and
- (e) Using supernatant from the hybridoma of (d) in a fusion screen under conditions suitable for isolating the monoclonal antibody.

13. The method of claim 9, wherein the cells of (c) are lymphocytes or splenocytes.

14. The method of claim 10, wherein the cells of (c) are lymphocytes or splenocytes.

15. The method of claim 11, wherein the cells of (c) are lymphocytes or splenocytes.

16. The method of claim 12, wherein the cells of (c) are lymphocytes or splenocytes.

* * * * *

UNITED STATES PATENT AND TRADEMARK OFFICE

CERTIFICATE OF CORRECTION

PATENT NO. : 7,071,311 B2
APPLICATION NO. : 10/366191
DATED : July 4, 2006
INVENTOR(S) : Radka et al.

It is certified that error appears in the above-identified patent and that said Letters Patent is hereby corrected as shown below:

On the Title Page; Item (75)
Inventors, please delete current and replace with -

--Susan Radka, Arvada, CO (US);
Leonid Beigelman, Longmont, CO (US);
Peter Haeberli, Berthoud, CO (US)--

Signed and Sealed this

Twenty-eighth Day of November, 2006

JON W. DUDAS
*Director of the United States Patent and Trademark Office*